(12) United States Patent
Ryali et al.

(10) Patent No.: US 8,765,447 B2
(45) Date of Patent: Jul. 1, 2014

(54) **FUNGAL STRAIN *BEAUVERIA* SP. MTCC 5184 AND A PROCESS FOR THE PREPARATION OF ENZYMES THEREFROM**

(75) Inventors: Seeta Laxman Ryali, Maharashtra (IN); Shiv Shankar, Maharashtra (IN); Snehal Vijay More, Maharashtra (IN); Harish Bansilal Khandelwal, Maharashtra (IN); Chandra Babu Kannan Narasimhan, Tamil Nadu (IN); Saravanan Palanivel, Tamil Nadu (IN); Padmanabhan Balaram, Karnataka (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/577,393

(22) PCT Filed: Feb. 4, 2011

(86) PCT No.: PCT/IB2011/000178
§ 371 (c)(1), (2), (4) Date: Nov. 23, 2012

(87) PCT Pub. No.: WO2011/095875
PCT Pub. Date: Aug. 11, 2011

(65) Prior Publication Data
US 2013/0095523 A1 Apr. 18, 2013

(30) Foreign Application Priority Data
Feb. 5, 2010 (IN) .............................. 249/DEL/2010

(51) Int. Cl.
*C12N 1/14* (2006.01)
(52) U.S. Cl.
USPC ....................................... 435/254.1; 435/911
(58) Field of Classification Search
None
See application file for complete search history.

(56) References Cited

PUBLICATIONS

Agrawal et al. "Alkaline protease production by a soil isolate of *Beauveria* feline under SSF condition: parameter optimization and application to soy protein hydrolysis". Process Biochemistry. 2005, 40, pp. 1131-1136.*

Agrawal, D et al., "Alkaline protease production by a soil isolate of *Beauveria* feline under SSF condition: parameter optimization and application to soy protein hydrolysis", Process Biochemistry, Mar. 1, 2005, vol. 40, No. 3-4, pp. 1131-1136.

* cited by examiner

*Primary Examiner* — Vera Afremova
(74) *Attorney, Agent, or Firm* — Arent Fox LLP

(57) ABSTRACT

A fungal strain *Beauveria* species bearing accession number MTCC 5184 is disclosed. The process for the preparation of an enzyme mix including at least one enzyme selected from, but not limited to protease, carbohydrase, and lipase from the disclosed *Beauveria* species and uses of the enzyme mix in various areas also disclosed.

1 Claim, 10 Drawing Sheets

Figure 3:
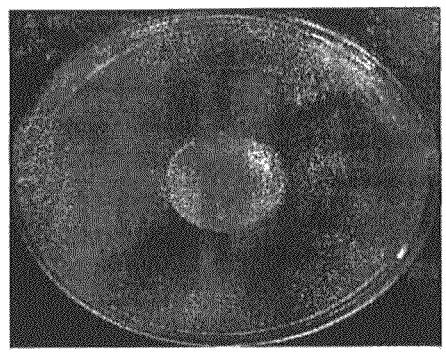

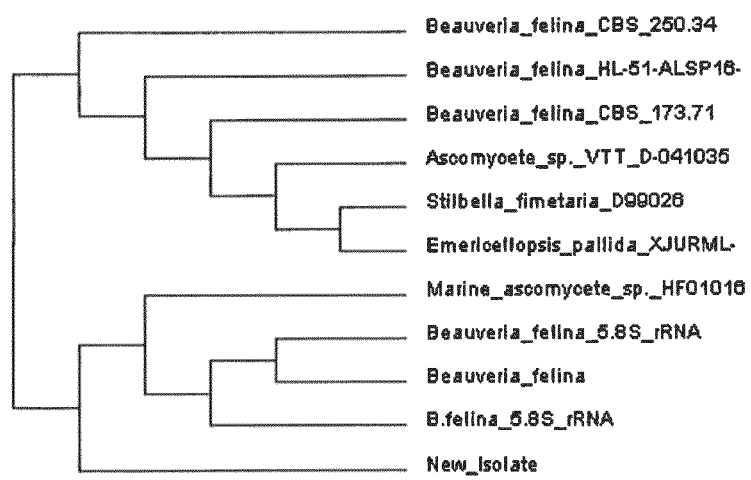
Figure 1
 
Figure 2a          Figure 2b

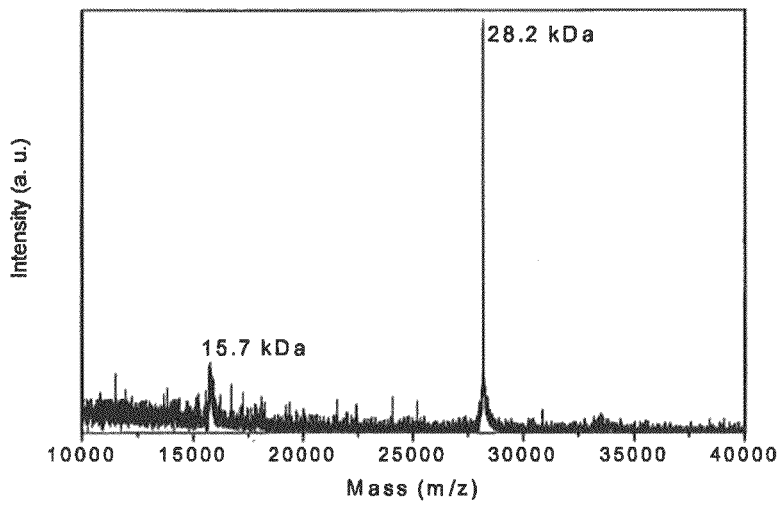

Figure 7

```
New strain of Beauveria sp        -                                              AMATPHVAPLVLYGVA
Magnaporthe poae - Subtilisin like protease - sp|Q9Y778.1|SMP1_MAGPO             MATPHVSGLVLY
A. niger - subtilisin-like serine protease pepD - ref|XP_001393694.1|            MATPHVTGLILY
Verticillium dahliae - subtilisin-like protease - gb|AAR10769.1|                 MASPHVAGLVVY
Metarhizium anisopliae - subtilisin-like protease PR1D - emb|CAB63914.1|         MASPHVAGLALY
Acremonium chrysogenum - alkaline protease - dbj|BAA00765.1|                     MATPHVTGVVLY
Epichloe festucae - subtilisin-like protease - gb|ACB30133.1|                    MATPHVVGLALY
Neotyphodium lolii -  subtilisin-like protease - gb|ACB30130.1|                  MATPHVVGLALY
Hypocrea lixii - serin endopeptidase - emb|CAL25580.1|                           MATPHVVGLALY
Trichoderma hamatum- alkaline proteinase - gb|AAP15044.1|                        MATPHVVGLALY
Hypocrea virens - extracellular serine protease; Tvsp1 - gb|AAO63588.1|          MATPHVVGLALY
Pseudoalteromonas flavipulchra - serine protease - gb|ABR01160.1|                MATPHVAGAAALVL
Hypsizygus marmoreus - serine protease - gb|ABL98208.2|                          MATPHIAGLVAY
```

Figure 8

FUNGAL STRAIN *BEAUVERIA* SP. MTCC 5184 AND A PROCESS FOR THE PREPARATION OF ENZYMES THEREFROM

CROSS-REFERENCED TO RELATED APPLICATIONS

This application is a National Stage entry of International Application PCT/IB2011/000178, filed Feb. 4, 2011, which claims priority to Indian Patent Application No. 249/DEL/ 2010, filed Feb. 5, 2010. The disclosures of the prior applications are hereby incorporated in their entirety by reference.

SEQUENCE LISTING

The instant application contains a Sequence Listing which has been submitted in ASCII format via EFS-Web and is hereby incorporated by reference in its entirety. Said ASCII copy, created on Oct. 18, 2012, is named 26330050.txt and is 6,005 bytes in size.

FIELD OF INVENTION

The present invention relates to a novel fungal strain *Beauveria* sp. MTCC 5184 and a process for the preparation of enzymes therefrom. In particular, the present invention relates to a composition of enzymes comprising protease, lipase and carbohydrase from *Beauveria* species, MTCC 5184. Further the invention relates to a process for preparation of said composition and uses thereof.

BACKGROUND OF INVENTION

The current estimated value of worldwide sales of industrial enzymes is $1 billion. Of the industrial enzymes, 75% are hydrolytic. Proteases, amylases, lipases and xylanases together constitute around 85-90% total enzyme sales out of which proteases from plant, animal and microbial sources account for about 60%.

Bacterial proteases are well known, fungal source of proteases are limited though advantageous. Further fungal source of proteases in combination with other enzymes are also limited.

An article titled "Action of enzymatic systems of *Beauveria bassiana* on the cuticle of the greater wax moth larvae (*Galleria mellonella*)" by J. Leopold et. al; published in Journal of Invertebrate Pathology, Volume 18, Issue 3, November 1971, Pages 322-330 discloses that the entomogenous fungus *Beauveria bassiana* (Deuteromycetes) secretes into the nutrient medium a mixture of at least three enzymes, lipase, protease and chitinase; which enables penetration of the fungus through the cuticle of the infested insect.

An article titled "Purification and characterization of a novel extracellular protease from *Beauveria bassiana*" by B. E. Urtz and W. C. Rice; published in Mycological Research (2000), 104:180-186; discloses an extracellular protease designated BBP (*Beauveria bassiana* protease) purified from a *B. bassiana* isolate. Substrate specificity indicates that the protease has elastase activity as well. The protease was stable at 25° C. and had an alkaline pH optimum (7.5-9.5).

An article titled "Alkaline protease production by a soil isolate of *Beauveria felina* under SSF condition: parameter optimization and application to soy protein hydrolysis" by Deepti Agrawal et. al; Process Biochemistry, Volume 40, Issues 3-4, March 2005, Pages 1131-1136 having doi: 10.1016/j.procbio.2004.03.006; discusses alkaline protease activity of a soil isolate of *Beauveria felina* for soy protein hydrolysis and compares it with *Aspergillus oryzae* NCIM 649, a known alkaline protease producer, under solid substrate fermentation (SSF) condition. The parameters affecting alkaline protease production under SSF condition were optimized.

But there is no prior art relating to production of amylases, keratinases and xylanases alone or in combination with alkaline proteases by *Beauveria* species.

Further applications of enzyme compositions in biomass, crude, refined, purified or any such forms are hitherto unknown from *Beauveria* species.

OBJECTS OF THE INVENTION

The main object of the present invention is therefore to provide a species of *Beauveria* that is capable of providing an enzyme composition that is capable of being applied in various areas.

Another object of the invention is to provide a composition comprising of at least one or more of the following enzymes: protease, amylase, lipase, xylanase, chitinase and keratinase from a fungal source, a hitherto unknown strain of *Beauveria* sp.

Still another objective of the invention is to provide a process for the preparation of an enzyme composition containing at least one or more of the following enzymes: protease, amylase, lipase, xylanase, chitinase and keratinase using a fungal culture belonging to genus *Beauveria* isolated by the inventors.

Yet another objective of the present invention is to provide a process for the preparation of an alkaline protease which is active and stable in wide pH range and in short fermentation cycles.

Still another objective of the present invention is to provide an economical process for the production of protease, amylase, lipase, xylanase, chitinase and keratinase alone or in combination.

A further objective of the invention is to provide applications/use of the said enzymes in animal tissue culture, analytical tools, pharmaceutical, molecular biology, leather, detergent, food, textile, and such like industries.

SUMMARY OF THE INVENTION

A novel species of *Beauveria* i.e. *Beauveria* MTCC-5184 is disclosed herein. A composition comprising at least one enzyme selected from, but not limited to protease, carbodydrase and lipase prepared from the said fungal source is also disclosed. The process of preparation of the said enzyme composition and applications/uses thereof are also described.

More specifically, the invention pertains to alkaline protease, lipase and carbohydrase active and stable over wide pH range and stable in presence of various detergents, organic solvents, denaturants etc which have potential applications in animal tissue culture, leather, food, detergent and other industries.

Accordingly, the present invention provides a fungal strain *Beauveria* species bearing accession number MTCC 5184, wherein the said strain is deposited at MTCC, an International Depository recognized under the Budapest Treaty.

The invention further provides a process for preparation of the enzymes comprising at least one enzyme selected from, but not limited to protease, carbohydrase and lipase from *Beauveria* species bearing accession number MTCC 5184, said process comprising:

[a] culturing *Beauveria* species MTCC 5184 in a medium comprising 0.15 to 80% of a carbon source, 0.15 to 80% of a nitrogen source and an inducer under aerobic conditions at pH ranging from 5.0 to 9.0 and temperature ranging between 15° to 32° C. for a period ranging between 2 to 7 days;

[b] harvesting the medium as obtained in step (a); and

[c] separating/extracting the enzymes in liquid phase by conventional methods.

BRIEF DESCRIPTION OF THE ACCOMPANYING DRAWINGS

FIG. 1: Dendrogram showing homology on the basis of multiple sequence alignment of Internal transcribed space (ITS) sequences. ITS sequence of new isolate shows maximum homology with *Beauveria felina* sequences.

FIG. 2a: Morphology of *Beauveria felina* (NCIM 1314)

FIG. 2b: Morphology of new isolate. There are marked differences in the morphology, specifically the presence of erect stalks (synnemata) in the new isolate.

FIG. 3: Plate assay showing production of lipase by *Beauveria* sp MTCC 5184. Clearance zone around the growing *Beauveria* colony on medium containing tributyrin indicating secretion of lipase by the fungus.

FIG. 4: Plate assay showing production of chitinase by *Beauveria* sp MTCC 5184. Clearance zone on acid swollen chitin plate around the spot where culture filtrate was placed indicating secretion of chitinase by the fungus.

FIG. 5*a*: Depicts stability of protease spray dried in presence of 10% Maltodextrin and FIG. 5*b*: Depicts stability of protease spray dried in presence of 15% Maltodextrin.

FIG. 6: Cationic polyacrylamide gel electrophoresis (PAGE) of purified protease showing (6*a*) single protein band after silver staining and (6*b*) corresponding band showing gelatin clearance after activity staining.

FIG. 7: MALDI-TOF of purified protease showing a major peak with molecular weight 28.2 kDa FIG. 8: Multiple sequence alignment (SEQ ID NOS 11 and 14-25, respectively, in order of appearance) of N-terminal sequence of purified protease from new strain of *Beauveria* with protein sequences of other organisms which shows partial sequence similarity with few proteases from other organisms.

FIG. 9: Kinetics of inhibition of protease with phenyl methyl sulfonyl fluoride (PMSF): Inhibition is linear with incubation time and increased with concentration of PMSF FIG. 10: Stability of protease at 37° C. in presence of water miscible solvents. Protease was most stable in presence of methanol (retained >80% initial activity) followed by ethanol, isopropanol and acetone while control retained around 30-35% of initial activity.

FIG. 11: Stability of protease at 37° C. in water immiscible solvents. Protease was stable in all the water immiscible solvents and retained 50-80% activity after 24 h.

FIG. 12: Effect of urea concentration on stability of protease. Protease was stable in presence of urea and showed slight increase in stability with increasing concentration of urea.

FIG. 13: Stability of protease in presence of 3M NaCl and 6M urea. After 2 h incubation, protease retained more than 85% activity in presence of 6M urea and 75% activity in presence of 3M NaCl and 67% in control of initial activity.

FIG. 14: Effect of NaCl concentration on stability of protease. Protease showed 100% stability in the presence of 3 M NaCl.

FIG. 15: UV-Vis spectra showing presence of silver nanoparticles in solution. Peaks at 280 nm and near 400 nm are due to presence of protein and silver nanoparticles respectively.

FIG. 16: Microphotographs of animal cells before and after treatment with protease. Cells are separated due to the action of protease.

FIG. 17: Figure showing removal of blood stains. Crude protease was able to remove blood stain along with blood clots while commercial detergent removed only stains.

DETAILED DESCRIPTION OF THE INVENTION

In accordance with the invention, a composition comprising at least one enzyme selected from, but not limited to protease carbohydrase and lipase from a fungal source, a hitherto unknown strain of *Beauveria* species is disclosed herein.

The fungal strain, *Beauveria* species was isolated from rabbit dung and bears accession number MTCC-5184 (Microbial Type Culture Collection, Chandigarh, India). The sources of *Beauveria* are soil, insect, animal dung, tree twigs, marine life and such like. The culture was isolated from rabbit dung. The dung pellets were placed on clean moist filter paper in a petri plate. The plate was kept in a moist chamber and incubated at room temperature for 2-3 weeks. Initially, there was a white fungal growth which on further incubation shows small protrusions which developed in to erect stalks. The spores from these stalks were lifted carefully with a sterile pointed needle and spread on malt extract, glucose, yeast extract, peptone (MGYP) agar plate. Isolated colonies were purified by repeated sub-culturing on MGYP plates and single colonies were transferred to MGYP slants. The isolates so obtained were characterized and distinguished from *Beauveria felina* using the 18S rDNA & ITS sequences and morphological characteristics. The results in the Table 1 and Table 2 show the first 10 BLAST hit of 18S rDNA and ITS sequence. 18S rDNA and ITS sequence showed 99% homology with different strains of *Beauveria felina*. FIG. 1 shows the sequence homology of ITS gene with the other organisms. According to the 18S rDNA and ITS sequence homology, the isolate of the invention shows 98-100% homology to *Beauveria felina*. However, as shown in FIG. 2 there are significant differences in its morphology compared to *Beauveria felina* (NCIM 1314). The 18S rDNA and ITS gene sequences of MTCC 5184, a new strain of *Beauveria* sp. has been deposited with NCBI gene bank with the accession numbers FJ895305 and FJ895306 respectively.

In one embodiment of the invention, the composition comprises enzymes selected from, but not limited to protease, keratinase, amylase, xylanase, chitinase and lipase either alone or in any combination.

In another embodiment of the invention, the enzyme composition is inert to true collagen.

In still another embodiment of the invention, the enzymes composition of the invention is in the forms selected from, but not restricted to of biomass, crude form, purified form, refined form, cell bound form or immobilized form.

In yet another embodiment of the invention, the enzyme composition is stable to physical processing generally applied to enzyme compositions such as drying, filtration, concentration, refinement and such like.

In still another embodiment of the invention, the present invention provides a process for the preparation of an enzyme composition using *Beauveria* species comprising of:

a. growing the fungal strain *Beauveria* MTCC 5184 in a medium comprising a carbon source, a nitrogen source and an inducer under aerobic conditions, pH ranging from 5.0 to 9.0, and temperatures ranging between 15° to 32° C., for periods ranging between 2 to 7 days;
b. harvesting the medium and
c. separating/extracting the enzyme in liquid phase by conventional methods.

In yet another embodiment of the invention, the organism is grown in submerged culture with shaking at 180 to 220 rpm.

In still another embodiment, the organism is grown in solid state fermentation under stationary conditions.

In another embodiment of the invention, the carbon sources comprise of, but are not restricted to sugars, sugar alcohols, polysaccharides, oils, fats, lipids, agricultural products/wastes and such like, alone or in combinations thereof. The sugars are glucose, fructose, arabinose, sucrose, lactose and such like; sugar alcohols are glycerol, mannitol, sorbitol and such like; polysaccharides are starch, xylan and such like; oils/fats are olive oil, sunflower oil, soyabean oil, gingelly oil, mustard oil, castor oil, coconut oil ground nut oil, tributyrin and such like and agricultural products/wastes are soya flour, potato waste, maize flour, soyabean meal, ground nut meal, mustard seed cake, cotton seed cake, wheat bran, corn cob, corn meal, rice bran and such like; chitin containing wastes like crab shells and such like.

In yet another embodiment of the invention, the nitrogen source is optionally organic or inorganic, alone or in combinations thereof. The inorganic nitrogen sources are selected from, but not limited to di-ammonium hydrogen phosphate, sodium nitrate, potassium nitrate and urea.

In still another embodiment of the invention, the organic nitrogen sources are selected from, but not limited to peptone, tryptone, soyatose, soyapeptone, casamino acids, casein, meat extract, beef extract, yeast extract, corn steep liquor and nitrogen-rich leguminous substrates exemplified by soya flour, soyameal, gram flour, mung flour, mustard seed cake, cotton seed cake, ground nut meal and such like, wastes from dairy, poultry, meat and food processing, keratin rich wastes like hair, feathers, wastes from fisheries and other wastes alone or in combinations thereof.

In yet another embodiment of the invention, the conventional methods of separating enzymes are filtration, centrifugation or extraction with water or dilute surfactants.

In still another embodiment of the invention, the inducers are selected from, but not limited to peptone, tryptone, soyatose, soyapeptone, casamino acids, casein, meat extract, beef extract, yeast extract, corn steep liquor and nitrogen-rich leguminous substrates exemplified by soya flour, soyameal, gram flour, mung flour, mustard seed cake, cotton seed cake, ground nut meal and such like, wastes from dairy like whey, poultry, food processing, meat and fish exemplified by fish meal and chicken feathers, feather meal and such like, agricultural wastes, exemplified as oil seed cakes, and carbohydrate wastes like waste cereals/grains, wheat bran, corn cob, corn meal, rice bran, oils, fats, tannery wastes like fleshings, trimmings and chrome shavings, keratin rich substrates like nails, hoofs, hair alone or in combinations thereof.

In a further embodiment of the invention, the inducers could be a source of carbon. In another embodiment the inducers could be a source of nitrogen for the process of producing the enzyme composition comprising at least one enzyme selected from lipase, protease and carbohydrase.

In another embodiment of the invention, the concentration of the enzymes was achieved either by membrane filtration or by salting out through addition of salts such as ammonium sulphate, sodium sulfate, sodium chloride etc., addition of organic solvents such as ethanol, acetone or by freeze drying or spray drying.

In still another embodiment of the invention, the protease of the invention is stable in the pH range of 3-11, preferably pH 7, stable to detergents, denaturants, water miscible and water immiscible organic solvents, and stable up to 50° C. The protease is active in the temperature range of 30 to 70° C., preferably at 50° C. and in the pH range of 5.5-12, and in presence of chelators, metal ions.

In yet another embodiment of the invention, the crude as well as purified protease shows activity towards albumin, haemoglobin, keratin, elastin-orcin, azocasein, azocoll and gelatin.

In still another embodiment of the invention, the protease was serine protease and inhibited by phenyl methyl sulphonyl fluoride (PMSF).

In another embodiment of the invention, the amylase is active in the pH range of 4 to 8 preferably at pH 6 and temperature range of 20 to 70° C. preferably at 45° C.

In still another embodiment of the invention, xylanase is active in pH range of 4 to 9 preferably at pH 6 and temperature range of 30 to 70° C. preferably at 50° C.

In yet another embodiment of the invention, lipase is active in the pH range of 4 to 9 preferably at pH 7 and temperature range of 20 to 60° C. preferably at 50° C.

In another embodiment of the invention, the enzyme composition is inert to true collagen.

The protease activity has been expressed in terms of tyrosine equivalents. The reaction mixture contained an aliquot of suitably diluted enzyme solution and 10 mg Hammerstein casein in 0.1 M sodium carbonate buffer pH 9.0 in a total volume of 2 ml. After incubation at 50° C. for 10 min, the reaction was terminated by the addition of 3 ml of 5% trichloroacetic acid (acidified with concentrated hydrochloric acid). The precipitate formed was filtered through Whatman No. 1 filter paper after standing for 30 min at room temperature. The absorbance of trichloroacetic acid soluble fraction was measured at 280 nm. Micrograms of tyrosine produced was calculated from a pre-calibrated graph of absorbance at 280 nm against tyrosine concentration and the units are expressed as moles of tyrosine released per minute under assay conditions.

The xylanase activity was measured using 1% soluble xylan in 50 mM potassium phosphate buffer pH 6. The total reaction mixture of 1 ml contained 0.5 ml of suitably diluted enzyme and 0.5 ml substrate and incubated at 50° C. for 30 min. The reducing sugar liberated was measured by dinitro salicylic acid method (P. Bernfeld 1955, Amylase: α & β, Methods in Enzymology, Volume 1, 149). Xylanase activity was expressed as μmoles of reducing sugar (as xylose equivalents) produced per min under the assay conditions.

The amylase activity was measured using 1% soluble starch in 50 mM potassium phosphate buffer pH 6. The total reaction mixture of 1 ml contained 0.5 ml of suitably diluted enzyme and 0.5 ml substrate and incubated at 45° C. for 30 min. The reducing sugar liberated was measured by dinitro salicylic acid method (P. Bernfeld 1955, Amylase: α & β, Methods in Enzymology, Volume 1, 149). The amylase activity is expressed as μmoles of reducing sugar (as glucose equivalents) produced per min under the assay conditions.

Lipase activity was measured by two different methods.
a. Spectrophotometric assay using p-nitro phenol palmitate (pNPP) as substrate: The substrate solution was freshly prepared by drop wise addition of 1 ml of solution A (30 mg pNPP in 10 ml of propane-2-ol) to 9 ml of Solution B (0.1 g gum arabic and 0.4 g Triton-X-100 in 90 ml distilled water) with constant stirring. The emulsion remained stable for 2 h. The assay mixture contained 0.9 ml substrate, 0.1 ml 50 mM phosphate buffer pH 7 and 0.1 ml suitably diluted enzyme. The assay mixture was incubated at 28° C. for 20 min and terminated by addition of 2 ml of 2% $Na_2CO_3$. The amount of p-nitrophenol released was measured at 410 nm. The lipase activity is expressed as µmoles of p-nitro phenol released per min under the assay conditions.

b. Titrimetric assay of Lipase: The substrate was prepared by mixing 20 ml of olive oil, 165 ml of 10% gum arabic and 15 g ice in grinder mixer for 10 minutes and filtered on glass wool and stored at 4° C. For lipase assay the reaction mixture contained 2 ml phosphate buffer (50 mM, pH 7.0), 5 ml substrate and 1 ml crude culture broth and incubated at 50° C. for 1 h with shaking at 50 rpm. The reaction was terminated by addition of 4 ml of acetone:ethanol (1:1). In blank the enzyme was added after the termination of reaction by acetone:ethanol. Free fatty acids released were titrated with 10 mM NaOH. The lipase activity is expressed as µmoles of free fatty acids released per min under the assay conditions.

The enzyme composition of the invention finds use in all fields where there is a need for enzyme based composition, including food, pharmaceutical, leather, textile industries. Proteases find application in agriculture, leather, textile, degumming of silk, dairy, food, feed, detergent, pharmaceutical industries, fertilizer, preparation of media ingredients and protein hydrolysates from plant, animal, peptide synthesis, in molecular biology, cosmetics, waste treatment and such like. Lipases find application in agriculture, leather, textile, dairy, food, feed, detergent, pharmaceutical industries, fertilizer, cosmetics, waste treatment, polymer synthesis and such like. Amylases find application in agriculture, leather, textile, food, feed, detergent, pharmaceutical industries, preparation of media ingredients, waste treatment, etc. Xylanases find application in agriculture, paper and pulp, leather, textile, food, feed, pharmaceutical, waste treatment, single cell protein, fuels, solvents, synthesis of oligosaccharides, degumming of fibers like hemp, jute, ramie, flax etc, debarking, etc. Traditionally, keratinases have been used for production of feather meal, fertilizers and glues etc. Their application range is slowly widening and now they are increasingly being used in to other areas such as detergent formulation, cosmetics, leather, medicine and animal feed. More recently, they find applications in treatment of mad cow disease (degradation of prion), biodegradable plastic and feather meal production. Application of keratinases having mild elastolytic activity but lacking collaginolytic is being explored for the dehairing process in leather manufacture.

Use of enzyme composition comprising at least one enzyme selected from, but not limited to protease amylase, xylanase, chitinase, keratinase and lipase from *Beauveria* species for pre-tanning operations like dehairing in leather manufacture, animal cell culture, recovery of silver from photographic film, and nanoparticle synthesis, peptide synthesis in organic solvents and detergent compositions. Such detergent compositions are capable of stain removal.

Conventional method of unhairing process result in the discharge of effluent with high organic nitrogen, biological oxygen demand (BOD), chemical oxygen demand (COD) and total dissolved solids (TDS) and increased pH that pollutes the soil as well as the ground water and therefore cause irreversible damage to ecosystem. Dehairing with alkaline proteases result in significant reduction in both quantity of wastewater and in the pollution load. In addition, amylases, particularly in combination with proteases, are useful in to bating operation of the beam house (U.S. Pat. No. 4,273,876).

The enzyme composition of the invention is useful to leather industry for various pre-tanning operations. Particularly the composition is used in pre-tanning operations alone. More particularly the enzyme composition of the invention offers a chemical additive free option for pre-tanning operation to the leather industry as exemplified herein. This eco-friendly process involves the use of proteolytic enzymes replacing lime and sulphide in unhairing thereby resulting in the reduced BOD, COD and TDS in the effluent. These enzymes can be used in leather processing at pH range of 6-8.

Unlike the conventional method where the hair itself is destroyed totally by the use of solid sulphide and calcium hydroxide, the enzymatic process results in the removal of epidermal layer so that the hair is loosened or remove at its root.

EXAMPLES

The present invention is described herein below with examples, which are illustrative only and should not be construed to limit the scope of the present invention in any manner whatsoever.

Example 1A

This example illustrates the isolation of genomic DNA of *Beauveria* sp MTCC 5184 by cetyl trimethyl ammonium bromide (CTAB) method. For isolation of DNA, the fungus was grown in liquid flasks in malt extract glucose yeast extract peptone (MGYP) medium the composition of which is (grams per liter) malt extract-3; yeast extract-3; peptone-5 and glucose-10. Growth was initiated by inoculating spores from a 7 day old MGYP slant. The flasks were incubated on a rotary shaker (200 rpm) for 48 hours at 28° C. The contents were centrifuged at 8000 rpm for 15 min, washed repeatedly to remove the media constituents. 3-5 g of wet mycelium was ground in liquid nitrogen, followed by addition of 8-10 ml of CTAB extraction buffer, pH 8 containing 0.2% 1'-mercaptoethanol after which 20 µl of proteinase K (20 mg/ml) was added and incubated at 65° C. for 1 h. This was followed by addition of 20 µl RNase A (10 mg/ml) and further incubation at 65° C. for 15 min. To the supernatant collected after centrifugation (8000 rpm, 10 min), 10 ml chloroform:isoamylalcohol (24:1) was added. The mixture was shaken for 5 min and centrifuged at 10,000 rpm, 4° C. for 15 min. Two volumes of CTAB precipitation buffer, was added to the supernatant and kept at room temperature for 1 h. The pellet collected after centrifugation was dissolved in 5 ml of 1.2 M NaCl and 5 ml of chloroform:isoamylalcohol (24:1) was added. Two volumes of absolute alcohol was added to the aqueous phase to precipitate the DNA. DNA was spooled out and washed with 70% ethanol and dissolved in 5 ml of 0.1M Tris ethylene-diaminetetraacetic acid (EDTA) buffer pH 8.0 and stored. The quantification of DNA was done by measuring the absorbance of the sample at 260 nm on spectrophotometer and purity was checked on 0.8% agarose gel electrophoresis.

Example 1B

This example illustrates the polymerase chain reaction (PCR) amplification of genomic DNA for 18S rDNA and internal transcribed spacer (ITS) gene. The primers used for the identification of fungal species were universal fungal 18S rDNA primers NS1-F (GTA GTC ATA TGC TTG TCT C (SEQ ID NO: 1)), NS8-R (TCC GCA GGT TCA CCT ACG GA (SEQ ID NO: 2)), ITS1-F (TCC GTA GGT GAA CCT GCG G (SEQ ID NO: 3)) and ITS4-R (TCC TCC GCT TAT TGA TAT GC (SEQ ID NO: 4)). The polymerase chain reaction (25 µl) was set to amplify the 18S rDNA and ITS gene by using the genomic DNA. The reaction mixture typically contained genomic DNA-0.70 μl, 10×PCR Buffer-2.50 μl 0.2 mM dNTPs-2.5 μl, forward and reverse primers 10-20 pmoles-1.25 μl each, distilled water-16.60 μl, and 1 unit of Taq DNA polymerse-0.20 μl. The PCR conditions for 18S rDNA and ITS gene amplification were: initial denaturation-95° C. for 3 min; followed by 35 cycles of 94° C. for 1 min, 57° C. for 30 sec, 72° C. for 2 min and final extension at 72° C. for 10 min. 51.11 of the above PCR amplified product was used to check the amplification on 1.0% agarose gel.

Example 1C

This example illustrates the purification of PCR amplified products. To 20 μl PCR amplified products, 12 μl of 20% PEG-NaCl (Polyethylene glycol-NaCl) solution was added and incubated at 37° C. for 30 min. It was then centrifuged at 12,000 rpm for 20 min. The supernatant was discarded and the pellet was washed twice with 70% ethanol and separated by centrifuging at 12,000 rpm for 20 min. The pellet was dried and dissolved in 10 μl of double distilled water and stored at −20° C.

Example 1D

This example illustrates the sequencing of the purified PCR products. The sequencing reactions were carried out using Taq DNA polymerase using the 'ABI PRISM Bigpye Terminator Cycle Sequencing Ready Reaction Kit' (Perkin Elmer Applied Biosystems Division, Foster City, Calif.) according to the manufacturer's protocol. This Kit contains the four ddNTPs with different fluorescence labels termed as BigDye Terminators. 41 PCR product and 3 pmol of the sequencing primer were used in a 20 μl sequencing reaction. The sequencing primers were NS1 (GTA GTC ATA TGC TTG TCT C (SEQ ID NO: 1)), NS2 (GGC TGC TGG CAC CAG ACT TGC (SEQ ID NO: 5)), NS3 (GCA AGT CTG GTG CCA GCA GCC (SEQ ID NO: 6)), NS4 (CTT CCG TCA ATT CCT TTA AG (SEQ ID NO: 7)), NS5 (AAC TTA AAG GAA TTG ACG GAA G (SEQ ID NO: 8)), NS6 (GCA TCA CAG ACC TGT TAT TGC CTC (SEQ ID NO: 9)), NS7 (GAG GCA ATA ACA GGT CTG TGA TGC (SEQ ID NO: 10)) and NS8 (TCC GCA GGT TCA CCT ACG GA (SEQ ID NO: 2)), ITS1 (TCC GTA GGT GAA CCT GCG G (SEQ ID NO: 3)) and ITS4 (TCC TCC GCT TAT TGA TAT GC (SEQ ID NO: 4)) for sequencing (White et al 1990). The sequencing reaction mixes were subjected to 25 cycles in a Perkin Elmer thermal cycler 9700. Each cycle consisted of 95° C. for 10 min, 50° C. for 5 min and 60° C. for 4 min. DNA sequencing was carried out on ABI 1500 Automated Sequencer, Example 1E This example illustrates the identification and phylogenetic relationship of new strain of Beauveria sp MTCC 5184 on the basis of 18S rDNA and ITS sequence obtained in above example. The sequences obtained were in small fragments and hence it was aligned properly by overlapping the sequences. Percentage homology and phylogenetic relationship of new strain of Beauveria sp. was done using existing sequences in NCBI database. The nucleotide sequence was analyzed with the GenBank database using BLAST program (www.ncbi.ncm.gov/blast). The results in the Table 1 and Table 2 show that the first 10 BLAST hit of 18S rDNA and ITS sequence in NCBI database respectively. 18S rDNA and ITS sequence showed 99% homology with different strains of Beauveria felina. The FIG. 1 shows the sequence homology of ITS with the other organisms. According to the 18S rDNA and ITS sequence homology, the present strain shows 98-100% homology to Beauveria felina. However, as shown in FIG. 2 there are significant differences in its morphology compared to Beauveria felina. The 18S rDNA and ITS sequences of MTCC 5184, a new strain of Beauveria sp. have been deposited with NCBI gene bank with the accession numbers FJ895305 and FJ895306 respectively.

TABLE 1

First 10 BLAST hit of 18S rDNA

| Sequences showing significant alignment | | Score (bits) | E value | Homology |
|---|---|---|---|---|
| AY261369.1 | Beauveria felina strain CBS 250.34 18S | 3157 | 0.0 | 99% |
| AY261367.1 | Beauveria felina strain HL-51-ALSP16-I003 18S | 3153 | 0.0 | 99% |
| AY261368.1 | Beauveria felina strain CBS 173.71 18S | 3145 | 0.0 | 99% |
| AY489693.1 | Stilbocrea macrostoma strain GJS73-26 18S | 2996 | 0.0 | 98% |
| AB023945.1 | Paecilomyces lilacinus gene for 18S | 2968 | 0.0 | 97% |
| AB237663.1 | Nectria cinnabarina genes for 18S | 2964 | 0.0 | 98% |
| AB067701.1 | Cordyceps sinensis gene for 18S | 2964 | 0.0 | 97% |
| AY357275.1 | Nectria curta strain UMB 39.01 18S | 2963 | 0.0 | 97% |
| AB003949.1 | Nectria cinnabarina gene for 18S | 2959 | 0.0 | 97% |
| AY249900.1 | Bionectria pityrodes strain CBS 246.78 18S | 2946 | 0.0 | 97% |

TABLE 2

First 10 BLAST hit of ITS

| Sequences showing significant alignment | | Score (Bit) | E value | Homology |
|---|---|---|---|---|
| AY261369.1 | Beauveria felina strain CBS 250.34 18S | 928 | 0.0 | 99% |
| EF495156.1 | Marine ascomycete sp. HF01016 18S | 918 | 0.0 | 99% |
| AY261367.1 | Beauveria felina strain HL-51-ALSP16-I003 18S | 911 | 0.0 | 99% |
| U18956.1 | Beauveria felina 5.8S rRNA gene and ITS 1 and 2 | 874 | 0.0 | 100% |
| U35286.1 | Beauveria felina 5.8S rRNA gene and ITS I and II | 857 | 0.0 | 97% |
| Z54106.1 | Beauveria felina 5.8S rRNA gene and ITS 1 and 2 | 857 | 0.0 | 97% |
| AY261368.1 | Beauveria felina strain CBS 173.71 18S rRNA gene, ITS1 | 776 | 0.0 | 94% |

TABLE 2-continued

First 10 BLAST hit of ITS

| Sequences showing significant alignment | Score (Bit) | E value | Homology |
|---|---|---|---|
| AM410612.1 *Ascomycete* sp. VTT D-041035 | 614 | 1e−172 | 88% |
| AY952467.1 *Stilbella fimetaria* D99026 | 553 | 3e−154 | 86% |
| EU045572.1 *Emericellopsis pallida* strain XJURML-3 | 547 | 1e−152 | 86% |

Example 2

This example illustrates the preparation of the protease by submerged fermentation using the strain *Beauveria* MTCC 5184. Fermentation was carried out in shake flasks in a medium containing (grams per liter): Glucose-10; Yeast extract-3, Mustard seed cake-20. Spore suspension from a 7 day old slant was used for preparing the seed culture, the composition of which is malt extract, 3; yeast extract, 3; peptone, 5 and glucose 10. This was incubated on a rotary shaker for 48 hours at 28° C. and was used to initiate the shake flask experiments. The flasks were incubated for 96 h at 28° C. on a rotary shaker (200 rpm). The activity in the cell free broth after 4 days was 12-15 IU/ml.

Example 3

This example illustrates the preparation of the protease by submerged fermentation using the strain *Beauveria* MTCC 5184. Spore suspension from a 10 day old slant was used for preparing the MGYP seed culture, the composition of which is (grams per liter): malt extract, 3; yeast extract, 3; peptone, 5 and glucose 10. The inoculum flasks were incubated on a rotary shaker for 48 hours at 28° C. and used to initiate the fermentation. Fermentation was carried out in shake flasks in glucose yeast extract medium containing (grams per liter): glucose, 10; yeast extract 3 with 2% fish meal as inducer and incubated for 48 h at 28° C. on a rotary shaker (200 rpm). The activities in the cell free broth after 3 days ranged between 9.9 to 10.6 IU/ml.

Example 4

This example illustrates the preparation of the protease by solid state fermentation using the strain *Beauveria* MTCC 5184. Spore suspension from a 7 day old MGYP slant was used for preparing the seed culture, the composition of which is malt extract, 3; yeast extract, 3; peptone, 5 and glucose 10. The inoculum flasks were incubated on a rotary shaker for 48 hours at 28° C. and used to initiate the fermentation. Solid state fermentation for protease production was carried out in 250 ml flasks containing 5 g wheat bran; 20 mg yeast extract, 1 g soyabean meal and mixed with 7 ml water. Three ml of vegetative inoculum was added to solid fermentation medium and mixed well and incubated at 30° C. under stationary conditions. After 96 h incubation, the semi-solid moldy Koji was extracted with 50 ml 0.1% Tween-80 by shaking at 200 rpm for 1 h. To ensure complete extraction of the enzyme from the solid substrate, two more extractions were carried out with 0.1% T-80. The enzyme obtained was assayed and activities ranging from 450-570 IU/g of soyabean meal and 75 to 95 IU/g dry solid were obtained in 96 h.

Example 5

This example illustrates the preparation of the xylanase by submerged fermentation using the strain *Beauveria* MTCC 5184. Spore suspension from a 10 day old slant was used for preparing the seed culture in MGYP medium, the composition of which is (grams per liter): malt extract, 3; yeast extract, 3; peptone, 5 and glucose 10. The inoculum flasks were incubated on a rotary shaker for 48 hours at 28° C. and used to initiate the fermentation. Fermentation was carried out in shake flasks in Mikami medium whose composition is (grams per liter): glucose, 1.5; yeast extract 1.5; peptone 5 and beef extract 5 containing 3 different inducers namely: 3% wheat bran; 1% xylan and 2% corn cob. The shake flasks were incubated at 28° C. for 48 h on a rotary shaker (200 rpm). The xylanase activities in the cell free broth after 2 days in all the above inducers ranged between 4-5.5 IU/ml.

Example 6

This example illustrates the preparation of the xylanase by solid state fermentation using the strain *Beauveria* MTCC 5184. Spore suspension from a 10 day old slant was used for preparing the MGYP seed culture, the composition of which is (grams per liter): malt extract, 3; yeast extract, 3; peptone, 5 and glucose 10. This was incubated on a rotary shaker at 28° C. for 48 hours and used to initiate the fermentation. Solid state fermentation for enzyme production was carried out in 500 ml flasks containing 9 g wheat bran mixed with 15 ml Mikami medium whose composition is (grams per liter): Glucose-1.5; yeast extract-1.5; peptone-5; beef extract-5 and incubated at 28° C. under static conditions up to 4 days.

At the end of fermentation, the semisolid moldy Koji was extracted with 100 ml 0.01% Tween-80 by shaking at 200 rpm for 1 h. To ensure complete extraction of the enzyme from the solid substrate, one more extraction was carried out with 50 ml of 0.01% T-80. The xylanase activities at the end of 3 and 4 days were 62.33 IU/g and 96.54 IU/g respectively.

Example 7

This example illustrates the preparation of the amylase by submerged fermentation using the strain *Beauveria* MTCC 5184. Spore suspension from a 10 day old slant was used for preparing the seed culture in Mikami medium, the composition of which is (grams per liter): glucose-1.5; yeast extract-1.5; peptone-5; Beef extract-5. The inoculum flasks were incubated on a rotary shaker for 24 hours at 28° C. and used to initiate the fermentation. Fermentation was carried out in shake flasks in Mikami medium containing 2% corn starch as inducer and incubated at 28° C. on a rotary shaker (200 rpm). The activities in the cell free broth after 4 days ranged between 3.5-4.5 IU/ml.

Example 8

This example illustrates the preparation of the lipase by submerged fermentation using the strain *Beauveria* MTCC 5184. Spore suspension from a 7 day old slant was used for preparing the seed culture, the composition of which is (grams per liter) malt extract, 3; yeast extract, 3; peptone, 5 and glucose 10. This was incubated on a rotary shaker for 24 h at 28° C. and was used to initiate the shake flask experiments. Fermentation was carried out in shake flasks in a medium adjusted to pH 5.5 containing (grams per liter): NaNO$_3$-0.5; MgSO$_4$-0.5; KCl-0.5; KH$_2$PO$_4$-2; yeast extract-1; bactopeptone-5; glucose-10. Following oils at 1% concentration were used as inducers for lipase production. Flasks were incubated at 28° C. on a rotary shaker for 4-5 days. The activity in the cell free broth was determined using p-nitrophenyl palmitate as substrate. (give assay protocol). Lipase activities were in the range of 0.12-0.17 IU/ml; castor oil (0.13 IU/ml), ground nut oil (0.13 IU/ml), gingelly oil (0.17 IU/ml), olive oil (0.12 IU/ml).

Example 9

This example illustrates the preparation of the lipase by submerged fermentation using the strain *Beauveria* MTCC 5184. Spore suspension from a 7 day old slant was used for preparing the Mikami seed culture, the composition of which is (grams per liter): peptone-5; Beef extract-5; Yeast extract-1.5; Glucose-1.5. This was incubated on a rotary shaker at 28° C. for 48 hours and was used to initiate the shake flask experiments. Fermentation was carried out in shake flasks in Mikami medium containing (grams per liter): peptone-5; Beef extract-5; Yeast extract-1.5; Glucose-1.5. Olive oil and tributyrin at 2% concentration were used as inducers for lipase production. Medium was adjusted to pH 7. The activity in the cell free broth after 3-4 days was determined by titrimetric method. Lipase activities in olive oil and tributyrin were in the range of 3-5 IU/ml.

Example 10

This example illustrates the preparation of the keratinase by submerged fermentation using the strain *Beauveria* MTCC 5184. Spore suspension from a 7 day old slant was used for preparing the seed culture in Mikami medium, the composition of which is (grams per liter): yeast extract-1.5; peptone-5; beef extract-5 and glucose-1.5. The inoculum flasks were incubated on a rotary shaker for 48 hours at 28° C. and used to initiate the fermentation. Fermentation was carried out in shake flasks in Mikami medium containing 2% chicken feather and 2% hair as two different inducers. The shake flasks were incubated for 72 h at 28° C. on a rotary shaker (200 rpm). Keratinase activity was determined according to Bressollier et al, (Applied Environmental Microbiology, Vol. 65 (6), 2570-2576, 1999. One unit of enzyme activity is defined as the amount of enzyme required to cause an increase in absorbance by 1.0 at 595 nm per min. Keratinase activities after 3 days in the cell free broth for feathers and hair were 0.26 and 0.30 U/ml respectively.

Example 11A

This example illustrates the detection of lipase activity using plate assay by the strain *Beauveria* MTCC 5184. Plate assay for enzyme was carried out in disposable petri-plate containing 25 ml Mikami medium which was composed of glucose (grams per liter):1.5; yeast extract-1.5; peptone-5; beef extract-5, agar-20 and 1% tributyrin. Spore suspension from a 7 day old slant was used for preparing the inoculum. The composition of inoculum medium was (grams per liter): yeast extract-3 and glucose-10. Forty eight hours old vegetative inoculum was spot inoculated on the plate and incubated at 28° C. for 72 h. A zone of clearance around the growing fungal colony due to the degradation of tributyrin was observed indicating secretion of lipase by the organism (FIG. 3).

Example 11B

Figure 4:
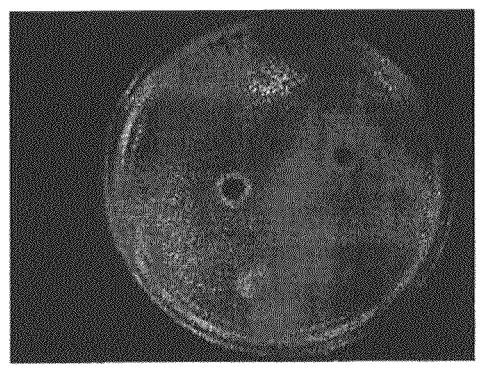

This example illustrates the detection of chitinase activity using plate assay by the strain *Beauveria* MTCC 5184. Plate assay was carried out in 25 ml of 2% agar containing 0.01% acid swollen chitin in disposable petri-plate. Spore suspension from a 7 day old slant was inoculated in medium the composition of which is (grams per liter): yeast extract-3, glucose-10 and acid swollen chitin-0.1 and incubated at 28° C. with shaking at 180-200 rpm. After 96 h, 50 µl of cell free supernatant was spotted on the plate and incubated at 37° C. for 1 h. For detection of chitinase activity, the plate was flooded with 0.1% ranipal for 15 min followed by two washings with distilled water for 30 min each. The plate was observed under UV light. A light blue clear zone around the sample spot was observed due to chitin degradation indicating secretion of chitinase by the fungal strain (FIG. 4).

Example 12

This example illustrates the simultaneous preparation of the amylase and protease by submerged fermentation using the strain *Beauveria* MTCC 5184. Spore suspension from a 7 day old slant was used for preparing the seed culture, the composition of which is (grams per liter): Glucose-1.5; Yeast extract-1.5, peptone-5, beef extract-5. This was incubated on a rotary shaker for 24 hours at 28° C. and 10% (v/v) of the inoculum was used to inoculate the experimental flasks. Fermentation was carried out in shake flasks in a medium adjusted to pH 7 containing (grams per liter): Glucose-1.5; Yeast extract-1.5, peptone-5, beef extract-5, starch-20. The flasks were incubated at 28° C. on a rotary shaker (200 rpm). The amylase and protease activities in the cell free broth after 6 days were 6-7 IU/ml and 3.0 to 3.3 IU/ml respectively.

Example 13

This example illustrates the preparation of the xylanase and protease by solid state fermentation using the strain *Beauveria* MTCC 5184. Spore suspension from a 10 day old slant was used for preparing the MGYP seed culture, the composition of which is (grams per liter): malt extract, 3; yeast extract, 3; peptone, 5 and glucose 10. This was incubated on a rotary shaker for 48 hours at 28° C. and used to initiate the fermentation. Solid state fermentation for enzyme production was carried out in 500 ml flasks containing 9 g wheat bran mixed with 9 ml Mikami medium whose composition is: Glucose-1.5; yeast extract-1.5; peptone-5; Beef extract-5.

At the end of fermentation, the semisolid moldy Koji was extracted with 100 ml of 0.01% Tween-80 by shaking at 200 rpm for 1 h. To ensure complete extraction of the enzyme from the solid substrate, one more extraction was carried out with 50 ml of 0.01% T-80. The xylanase and protease activities at the end of 4 days were 116-134 IU/g and 50-62 IU/g respectively.

Example 14

This example illustrates the preparation of the lipase and protease by solid state fermentation using the strain *Beauveria* MTCC 5184. Solid state fermentation for was carried out in 250 ml flasks in a medium containing 10 g wheat bran mixed with 1 g olive oil and 25 ml of basal salts medium adjusted to pH 5.5 the composition of which is (grams per liter): $NaNO_3$-0.5; $MgSO_4$-0.5; KCl-0.5; $KH_2PO_4$-2; yeast extract-1; bactopeptone-5. Two milliliters of spore suspension (1.75×10⁶ spores/ml) from 7 days old slant was used to inoculate the experimental flasks and incubated at 28° C. under static conditions. At the end of fermentation, the semi-solid moldy Koji was extracted with 100 ml 1% NaCl containing 0.1% Triton X-100 with shaking for 2 h followed by filtration through a double muslin cloth and centrifugation at 12000 rpm, 4° C. The activity in the cell free broth was determined using p-nitrophenyl palmitate as substrate. Lipase activities after 5 and 7 days were 0.8 IU/g and 5.115 IU/g respectively. Protease activity after 5 days was 45-48 IU/g Example 15

This example illustrates the simultaneous preparation of xylanase, amylase and protease by solid state fermentation using the strain *Beauveria* MTCC 5184. Solid state fermentation for enzyme production was carried out in 500 ml flasks containing 9 g wheat bran and 3 g starch and mixed with 15 ml Mikami medium which was composed of (grams per liter): glucose-1.5; yeast extract-1.5; peptone-5; beef extract-5. Spore suspension from a 10 day old slant was used for preparing the seed culture, the composition of which is (grams per liter): malt extract-3; yeast extract-3; peptone-5 and glucose-10. This was incubated on a rotary shaker for 48 hours at 28° C. and was used to initiate the fermentation.

After 120 h incubation, the semi-solid moldy Koji was extracted with 100 ml 0.01% Tween-80 by shaking at 200 rpm for 1 h. To ensure complete extraction of the enzyme from the solid substrate, one more extraction was carried out with 50 ml of 0.01% T-80.

At the end of 5 days, xylanase, amylase and protease activities per g wheat bran were 48-52 IU, 48-54 IU and 30-35 IU respectively.

Example 16

This example illustrates protease production in the temperature range of 15 to 37° C. by submerged fermentation using the strain *Beauveria* MTCC 5184. Spore suspension from a 7 day old slant was used for preparing the MGYP seed culture, the composition of which is (grams per liter): malt extract-3; yeast extract-3; peptone-5 and glucose-10. This was incubated on a rotary shaker at 28° C. for 48 hours and was used to initiate the shake flask experiments. Fermentation was carried out in shake flasks in a medium containing (grams per liter): Glucose-10; Yeast extract-3, Mustard seed cake-20 adjusted to pH 6.5-7. The flasks were incubated at temperatures ranging from 15 to 37° C. on a rotary shaker (200 rpm) for 96 h. Protease production was observed in the temperature range of 15 to 32° C. with highest activities at 28° C. (Table 3).

TABLE 3

Effect of Temp on protease production by *Beauveria* sp MTCC 5184

| Temperature (° C.) | Relative Activity (%) |
| --- | --- |
| 15 | 72.99 |
| 20 | 87.10 |
| 28 | 100 |
| 32 | 31.15 |
| 37 | 10.99 |

Example 17

This example illustrates the preparation of the protease by submerged fermentation in the pH range 5 to 9 using the strain *Beauveria* MTCC 5184. Spore suspension from a 7 day old slant was used for preparing the MGYP seed culture, the composition of which is (grams per liter): malt extract-3; yeast extract-3; peptone-5 and glucose-10. This was incubated on a rotary shaker at 28° C. for 48 hours and was used to initiate the shake flask experiments. Fermentation was carried out in shake flasks in a medium containing (grams per liter): Glucose-10; Yeast extract-3, Mustard seed cake-20. Medium pH was varied from pH 5 to 9. The shake flasks were incubated at 28° C. on a rotary shaker (200 rpm) for 96 h. Protease production was observed in the pH range 5 to 9 with highest activity at pH 7 (Table 4).

TABLE 4

Effect of pH on protease production by *Beauveria* sp MTCC 5184

| pH | Relative Activity (%) |
| --- | --- |
| 5.00 | 70.87 |
| 6.00 | 86.78 |
| 7.00 | 100.00 |
| 7.99 | 92.49 |
| 9.08 | 85.02 |

Example 18

This example illustrates the preparation of the protease by submerged fermentation in an instrumented fermentor under controlled conditions of agitation and aeration using the strain *Beauveria* MTCC 5184. Fermentation was carried out in 7.5 L New Bruinswick fermentor with working volume of 4 L and in a medium containing (grams per liter) Glucose-10; Yeast extract-3, Mustard seed cake-20 and adjusted to pH 7. Inoculum was developed in two stages in MGYP medium, the composition of which is (grams per liter) malt extract-3; yeast extract-3; peptone-5 and glucose-10 (MGYP). Spore suspension from a 7 days old slant was used for preparing the 1$^{st}$ stage inoculum. The first stage inoculum (24 h) was developed in 250 ml flasks containing 50 ml MGYP medium. The second stage inoculum (24 h) was developed in 1 L flasks containing 250 ml MGYP medium. The production medium (4 L) in 7.5 L fermentor contained glucose-yeast extract (GYE) as a basal medium. Mustard seed cake at a concentration of 2% was added as an inducer after 24 h of growth. Aeration and stirrer speed were kept at 3-4 liters per minute (lpm) and 350-400 rpm respectively and temperature was maintained at 26-28° C. The cell free broth was collected by gravity filtration on cotton. The activity in the cell free broth after 5 days was 12-15 IU/ml.

Example 19

This example illustrates the preparation of the protease by submerged fermentation in an instrumented fermentor under controlled conditions of agitation and aeration using the strain *Beauveria* sp. MTCC 5184. Fermentation was carried out in 100 L fermentor with working volume of 80 L and in a medium adjusted to pH 7 and containing (grams per liter) glucose-5; yeast extract-3; mustard seed cake-20 and 0.1% Tween-80. Inoculum was developed in two stages. The first stage inoculum was developed in 500 ml Erlenmeyer flasks containing 100 ml MGYP medium the composition of which is (grams per liter): malt extract-3; yeast extract-3; peptone-5 and glucose-10. Spores from 7-10 days old MGYP slant were inoculated and the flasks were kept shaking at 180-220 rpm for 24 h. The second stage inoculum was developed in a 14 L fermentor with a working volume of 10 L in GYE medium containing 1% glucose and 0.3% yeast extract pH was adjusted to 7. The fermentor was inoculated with 10% (v/v) inoculum from first stage. Aeration and stirrer speed were kept at 0.5 to 0.6 vvm and 350-400 rpm respectively and temperature was maintained at 26-28° C. The growth of inoculum was carried for about 12-24 h. and the contents were transferred to 100 L fermentor. The production medium (80 L) in 100 L fermentor was composed of (grams per liter): glucose-5; yeast extract-3; Tween-80-0.1%; mustard seed cake-20. Fermentation was carried out with an aeration of 60-80 liters per minute (lpm) and stirrer speed was adjusted between 100-250 rpm. The temperature of the fermentor was maintained at 26°-28° C. in order to obtain maximum yield. Fermentation was carried out for 3 to 4 days during which the pH increased to 8-8.3 and the enzyme was secreted into the medium. The fungal biomass was separated by centrifugation and the activity in the cell free broth after 4 days was 12-15 IU/ml.

Example 20

This example illustrates the production of amylase by solid state fermentation using the strain *Beauveria* MTCC 5184 and its concentration by ultrafiltration. Spore suspension from a 10 day old slant was used for preparing the MGYP seed culture, the composition of which is (grams per liter): malt extract-3; yeast extract-3; peptone-5 and glucose-10. This was incubated on a rotary shaker at 28° C. for 48 h and used to initiate the fermentation. Solid state fermentation for enzyme production was carried out in 1000 ml flasks containing 20 g wheat bran mixed with 10 ml of 10% Tween 80, 10 ml of Mikami medium whose composition is (grams per liter): Glucose-1.5; yeast extract-1.5; peptone-5; beef extract-5 and incubated at 28° C. under static conditions up to 5 days. At the end of fermentation, the semisolid moldy Koji was extracted with 150 ml of 0.01% Tween-80 by shaking at 200 rpm for 1 h. The amylase activities at the end of 5 days were 50 IU/g. The amylase so produced was centrifuged at 10,000 rpm. The clear supernatant was then concentrated in Amicon membrane filtration unit on PM-10 membrane with a molecular weight cut off of 10,000 daltons. The recovery after filtration was 95-98%.

Example 21

Figure 5A:
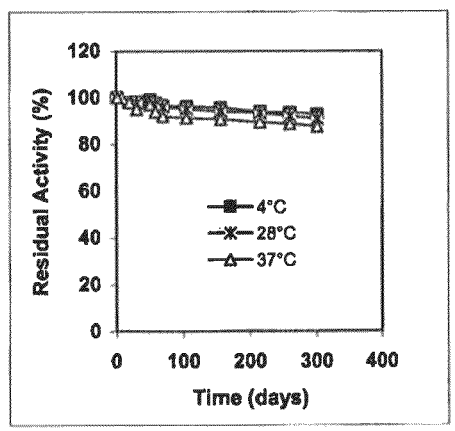
Figure 5B:
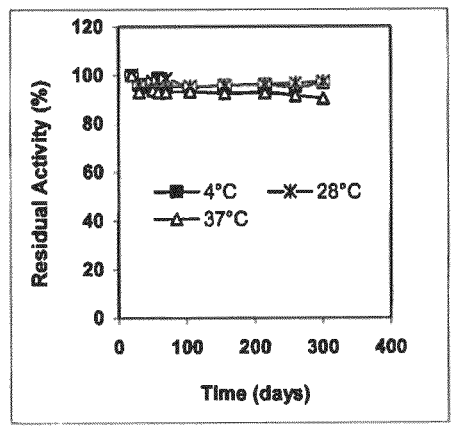

Crude protease produced as described in Example 18 was spray dried with 10% and 15% maltodextrin as additives with inlet temperatures of 150-160° C. and outlet temperatures of 60-65° C. and 70-80° C. respectively with 70-80% recoveries. The stability of spray dried protease was studied at temperatures ranging from 4° C. to 37° C. Samples were distributed in vials and stored at 4° C., 28° C. and 37° C. One vial incubated at each temperature was removed at regular intervals and residual activity was checked. Spray dried protease was stable up to 10 months (301 days) at all the temperatures tested and retained 90-95% activity (FIGS. 5a and 5b).

Example 22

Figure 6A:
Figure 6B:

This example illustrates the purification of the *Beauveria* sp MTCC 5184 protease to homogeneity. The fungus was grown on glucose-yeast extract medium containing 2% mustard seed cake for 4 days as described in Example 2 and the clear supernatant obtained after centrifugation at 10,000 rpm for 10 min was used as the source of enzyme. Fractional ammonium sulphate precipitation of the broth was carried out at 4° C. and dialyzed ammonium sulphate precipitate (40-70% saturation) was loaded on a diethyl aminoethyl cellulose (DEAE-cellulose) column (2.5 cm×25 cm) equilibrated with 50 mM phosphate buffer pH 7.0. The un-adsorbed enzyme was eluted with 50 mM phosphate buffer pH 7.0 at a flow rate of 20 ml/h. Fractions showing protease activity were pooled, concentrated by speed-vacc and stored at −20° C. Steps involved in purification are presented in accompanying Table 5 and forming the part of this specification. The purity of the enzyme preparation was checked on cationic polyacrylamide gel electrophoresis (PAGE) by visualizing protein bands after silver staining and protease bands after activity staining on X-ray film. Only a single protein band was seen after silver staining on cationic PAGE which corresponded to the activity band on X-ray film (FIG. 6).

TABLE 5

Summarization of purification of protease

| Purification steps | Total activity (U) | Total protein (mg) | Specific activity (U/mg) | Yield (%) | Purification fold |
|---|---|---|---|---|---|
| Crude culture filtrate | 9783 | 1624 | 6.025 | 100 | 1 |
| Ammonium sulphate (40-70%) | 6799 | 739.6 | 9.198 | 69.5 | 1.5 |
| DEAE-cellulose (Unbound fraction) | 3780 | 62.6 | 60.39 | 38.6 | 10.02 |

Example 23

This example confirms the purity of the unbound fraction obtained after DEAE-cellulose column chromatography. The pooled and concentrated sample as described in Example 12 was applied on TSK G 2000 SW pre-packed column of HPLC (7.5 mm×600 mm), eluted with 50 mM phosphate buffer, pH 7 at a flow rate of 0.7 ml/min which showed a single peak at retention time of 40 minutes.

Example 24

This example illustrates the determination of molecular weight of purified protease by sodium dodecylsulphate polyacryalmide gel electrophoresis (SDS-PAGE) and matrix-assisted laser desorption ionization time-of-flight (MALD-TOF). The molecular mass markers for SDS-PAGE consisted of carbonic anhydrase (29 kDa), fumarase (48.5 kDa), bovine serum albumin (66 kDa), phosphorylase b (97.4 kDa) and β-galactosidase (116 kDa). The molecular mass of the enzyme by SDS-PAGE was found to be around 29 kDa which corresponded to molecular weight of carbonic anhydrase.

The molecular mass of purified protease was also determined by using MALDI-TOF mass spectrometry using a Voyager DE-STR (Applied Biosystems) equipped with a 37-nm nitrogen laser. The purified enzyme was mixed with equal volume of sinapinic acid in acetonitrile and 20 μl of prepared sample was placed on MALDI plate for analysis. The purified enzyme showed the molecular weight of 28.2 kDa in MALDI-TOF which was nearly similar to the molecular weight of 29 kDa obtained by SDS-PAGE (FIG. 7).

Example 25

This example illustrates the determination of N-terminal sequence of purified protease. The purified enzyme was electrophoretically transferred from SDS-PAGE to a polyvinylidene difluoride membrane (PVDF) using semidry electroblotting unit. The protein was transferred in 3-cyclehexylamino 1-propane sulphonic acid (CAPS) buffer pH-11. To visualize band, the PVDF membrane was stained with Ponsue S. The region containing protease band on the PVDF membrane was excised and the protein N-terminal amino acid sequence was determined by the Edman degradation method on a Perkin Elmer sequencer, Procise (Applied Biosystems, Foster City, Calif., USA). The N-terminal sequence of the protease was found to be Ala-Met-Ala-Thr-Pro-His-Val-Ala-Pro-Leu-Val-Leu-Tyr-Gly-Val-Ala (SEQ ID NO: 11). This sequence did not show 100% homology with any of the proteases. Highest homology with 10 amino acids out of the 16 amino acids in the N-terminal sequence of the *Beauveria* sp MTCC 5184 protease was observed to subtilisin like protease. FIG. 8 shows the multiple sequence alignment of N-terminal amino acid of protease from new strain of *Beauveria* sp with other subtilisin like proteases.

Example 26

This example illustrates the in-gel trypsin digestion and peptide mass fingerprinting (PMF) of purified protease for its identification. The purified protease was run on 10% SDS-PAGE and stained with commassie brilliant blue (CBB). The stained SDS-PAGE band was excised and band was washed with 400 µl of 50% acetonitrile (3 times of 15 min each) to remove the CBB stain. The spots were dehydrated by using 100% acetonitrile for 10-15 min until the spots turn opaque white and then dried using speed vacuum. Protein band was then reduced and alkaylated by soaking in 100 µl of 10 mM dithiothreitol and then in 100 µl of 25 mM iodoacetamide. The band was then washed with 25 mM ammonium bicarbonate solution and digested with sequencing grade bovine trypsin (Sigma) solution. Molar ratio of protein to trypsin was maintained at 1:10. Peptides from the gel after overnight trypsin digestion were extracted with mixture of 50% acetonitrile and 5% trifluoroacetic acid (TFA), dried and stored at −20° C. till further analysis.

Peptides were reconstituted in 50 of 50% acetonitrile (ACN) containing 0.1% trifluoroacetic acid (TFA), then spotted and air dried on 96×2 Teflon coated plate. CHCA (γ-cyano hydroxy cinnamic acid) was added as a matrix onto the pre-spotted peptide spots. The Peptide mass fingerprinting (PMF) was obtained using a Voyager-DE-STR MALDI-TOF mass spectrometer. MALDI mass spectra were recorded in the mass range of 800-4000 Da. The protein was identified by using MASCOT database on the basis of peptide mass homology of tryptic digest. Out of 67 fragments taken for analysis, only 11 fragments match with subtilisin like protease 3 precursors from *Microsporum canis*.

Example 27

This example illustrates the determination of isoelectric point (pI) of the purified protease from *Beauveria* sp. MTCC 5184. Isoelectric focusing was carried out in 10% polyacrylamide gel in glass tube using ampholines in the range of pH 8.0-10.0 at 100 mV for 16 h. Two gels were cast and 100 µg of purified protease was added in each tube. The gels were taken out from glass tube, one of the gels was cut into 13 fractions of 1 cm each and another was stained with silver staining. Protease activity and pH of the fractions were checked. Isoelectric point of the protease was found to be 9.31.

Example 28

This example illustrates the effect of inhibitors on protease activity of *Beauveria* sp MTCC 5184. Following inhibitors were studied: phenylmethylsulfonyl fluoride (PMSF), ethylene-diaminetetraacetic acid (EDTA), iodoacetic acid, N-tosyl-L-phenylalanine chloromethyl ketone (TPCK), N-tosyl-L-lysine chloromethyl ketone (TLCK), Dimethylsulphoxide (DMSO) and Benzamidine. 300 µg of the purified protease was pre-incubated with each inhibitor in 100 mM Tris-HCl buffer (pH 8.0) for 1 h and the residual protease activity was measured 50° C., pH 9.0. Protease without inhibitor served as control. Protease was completely inhibited by 1 mM PMSF indicating it to be a serine protease (Table 6).

TABLE 6

Effect of inhibitors and chelators

| Inhibitor | Concentration | Inhibition (%) |
|---|---|---|
| Control | — | 0 |
| TPCK | 5 mM | 7.33 |
| TLCK | 5 mM | 12.12 |
| PMSF | 1 mM | 97.75 |
| EDTA | 20 mM | 1.51 |
| Iodoacetate | 10 mM | 0.30 |
| DMSO | 10% | 0.04 |
| Benzamidine | 5 mM | 3.62 |

Example 29

This example illustrates the effect of metal ions on protease activity of *Beauveria* sp MTCC 5184. Purified protease was incubated at 28° C. for 30 min with 1 mM and 10 mM chloride salts of different metals after which residual activity was checked. There was no activation of protease activity in presence of $Ca^{+2}$ indicating that the enzyme does not require calcium ion for its activity (Table 7). $Cu^{+2}$ and $Co^{+2}$ had no inhibitory effect on the protease while $Cd^{+2}$ and $Hg^{+2}$ showed <40% inhibition at 10 mM concentration. At 1 mM concentration, Cd and Hg showed 3% and 10% inhibition respectively.

TABLE 7

Effect of metal ions on protease activity

| | (Residual Activity (%)) | |
|---|---|---|
| Metal | 1 mM | 10 mM |
| None | 100.00 | 100.00 |
| $K^{+1}$ | 91.71 | 87.63 |
| $Na^{+1}$ | 100.94 | 99.01 |
| $Cu^{+2}$ | 109.42 | 100.02 |
| $Co^{+2}$ | 103.86 | 112.36 |
| $Cd^{+2}$ | 96.99 | 63.50 |
| $Mn^{+2}$ | 101.51 | 73.98 |
| $Hg^{+2}$ | 90.38 | 63.16 |
| $Ca^{+2}$ | 92.99 | 81.75 |
| $Fe^{+3}$ | 81.67 | 82.66 |

Example 30

Figure 9:
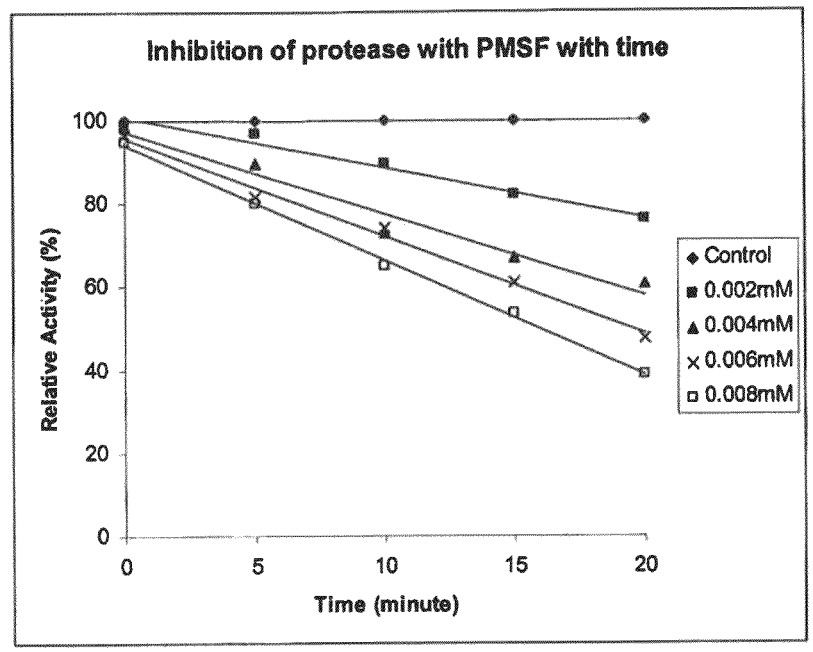
Figure 10:
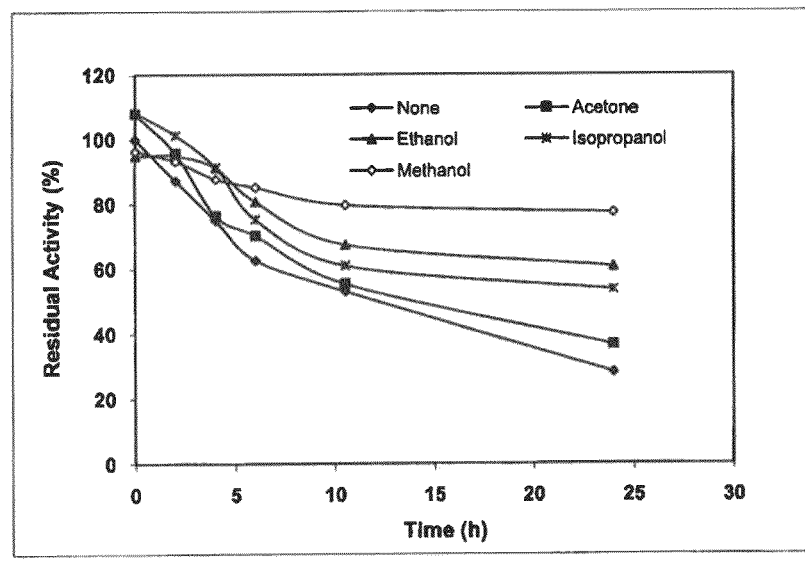

This example illustrates the modification of serine residue of protease by PMSF and its effect on protease activity. 10 µM of purified protease of *Beauveria* sp MTCC 5184 in 10 mM phosphate buffer, pH 7.0 was incubated with 0.005-0.05 mM PMSF at 28° C. for 30 min and residual activity was determined (Table 8). Protease incubated without PMSF served as the control. Complete inhibition was observed at 0.025 mM PMSF indicating the involvement of serine residue for the activity of protease. Inhibition kinetics with respect to concentration of PMSF and time are presented in FIG. 9.

TABLE 8

Chemical modification of serine with PMSF

| PMSF (mM) | Residual Activity (%) |
|---|---|
| 0 | 100.00 |
| 0.005 | 45.65 |
| 0.010 | 8.78 |
| 0.015 | 3.76 |
| 0.020 | 1.74 |
| 0.025 | 0 |
| 0.030 | 0 |
| 0.035 | 0 |
| 0.040 | 0 |
| 0.045 | 0 |
| 0.050 | 0 |

Example 31

This example illustrates the modification of aspartic acid residue of protease by Woodward's reagent (WRK) and its effect on protease activity. 10 μM of purified protease of *Beauveria* sp MTCC 5184 in 10 mM phosphate buffer, pH 7.0 was incubated with 1-10 mM WRK at 28° C. for 30 min and residual activity was determined. Protease incubated without WRK served as the control. Complete inhibition was observed at 9 mM WRK indicating the involvement of aspartic acid residue for the activity of protease (Table 9).

TABLE 9

Chemical modification of aspartic acid with WRK

| WRK (mM) | Residual Activity (%) |
|---|---|
| 0 | 100.00 |
| 1 | 86.08 |
| 2 | 75.76 |
| 3 | 61.47 |
| 4 | 49.05 |
| 5 | 34.66 |
| 6 | 19.53 |
| 7 | 11.69 |
| 8 | 6.39 |
| 9 | 0 |
| 10 | 0 |

Example 32

This example illustrates the modification of tryptophan with N-bromosuccinimide (NBS) and its effect on protease activity. 10 μM of purified protease of *Beauveria* sp MTCC 5184 in 10 mM phosphate buffer, pH 7.0 was incubated with 0.01-0.1 mM NBS at 28° C. for 30 min and residual activity was determined. Protease incubated without NBS served as the control. Complete inhibition was observed at 0.06 mM NBS indicating the involvement of tryptophan residue for the activity of protease (Table 10).

TABLE 10

Chemical modification of tryptophan with NBS

| NBS (mM) | Residual Activity (%) |
|---|---|
| 0 | 100.00 |
| 0.01 | 20.39 |

TABLE 10-continued

Chemical modification of tryptophan with NBS

| NBS (mM) | Residual Activity (%) |
|---|---|
| 0.02 | 15.70 |
| 0.03 | 12.55 |
| 0.04 | 8.93 |
| 0.05 | 7.08 |
| 0.06 | 0 |
| 0.07 | 0 |
| 0.08 | 0 |
| 0.09 | 0 |
| 0.10 | 0 |

Example 33

The example illustrates the study of substrate protection by casein on inhibition of *Beauveria* sp MTCC 5184 protease by PMSF, WRK and NBS. This was carried out by pre-incubating 10 μM of the purified protease with 1-10 mg of casein for 5 minutes at 4° C. followed by treatment with 10 μM PMSF, or 5 mM WRK or 10 μM NBS for 30 minutes and the residual protease activity determined. Increase in casein concentration decreased the inhibition by both the inhibitors indicating substrate protection by casein (Table 11). This indicates the presence of serine, aspartic acid and tryptophan at the active site of protease.

TABLE 11

Substrate protection by casein against inhibition by PMSF, NBS and WRK

| | Inhibition (%) | | |
|---|---|---|---|
| Casein (mg) | 0.01 mM PMSF | 0.01 mM NBS | 5 mM WRK |
| 0 | 95.02 | 87.06 | 75.26 |
| 1 | 74.91 | 84.85 | 66.03 |
| 2 | 70.78 | 69.95 | 59.32 |
| 3 | 64.06 | 64.09 | 53.22 |
| 4 | 60.71 | 48.93 | 45.06 |
| 5 | 52.65 | 43.25 | 40.25 |
| 6 | 45.22 | 38.03 | 31.10 |
| 7 | 41.73 | 34.06 | 26.27 |
| 8 | 34.80 | 24.25 | 19.32 |
| 9 | 31.56 | 16.27 | 12.87 |
| 10 | 26.26 | 16.28 | 8.72 |

Example 34

This example illustrates the determination of activity of the protease from *Beauveria* sp. MTCC 5184 towards casein, hemoglobin and bovine serum albumin. The reaction mixture contained an aliquot of suitably diluted protease enzyme and 10 mg substrate in 0.1M sodium carbonate buffer pH 9.0 in a total volume of 2 ml. After incubation at 50° C. for 10 min, the reaction was terminated by the addition of 3 ml of 5% trichloroacetic acid (acidified with concentrated hydrochloric acid). The precipitate formed was filtered through Whatman No. 1 filter paper after standing at room temperature for 30 min. The absorbance of trichloroacetic acid soluble fraction was measured at 280 nm. The protease is able to degrade the above substrates to varying degrees (Table 12).

TABLE 12

| | Activity towards substrates | |
|---|---|---|
| | Relative Activity (%) | |
| Substrate | Crude protease | Purified protease |
| Casein | 100.00 | 100.00 |
| Hemoglobin | 68.96 | 47.38 |
| BSA | 19.16 | 5.06 |

Example 35

This example illustrates the pH range in which the protease secreted by the said strain is active. For determination of optimum pH for protease, the enzyme was diluted and assayed in buffers of different pH ranging from 5.5 to 12. Following buffers were used: (0.1M). Citrate (pH 4 and 5) citrate phosphate buffer (pH 6), phosphate buffer (pH 7), Tris HCl buffer (pH 8) and carbonate bicarbonate (pH 9 and 10), sodium phosphate-NaOH (pH 11.0) and KCl—NaOH (pH 12.0). The results are presented in accompanying Table 13 and forming the part of this specification. It is observed that the enzyme is active between pH 5.5 and 12.

TABLE 13

| Optimum pH for Protease | |
|---|---|
| pH | Relative Activity (%) |
| 5.5 | 27.16 |
| 6 | 30.01 |
| 7 | 32.47 |
| 8 | 64.81 |
| 9 | 100.00 |
| 10 | 89.83 |
| 11 | 41.25 |
| 12 | 28.81 |

Example 36

This example illustrates the temperature range in which the protease secreted by the said strain is active. For determination of optimum temperature, protease activity was determined with carbonate bicarbonate buffer (0.1M, pH 9) at temperatures ranging from 30 to 70° C. The results of the experiment have been illustrated in Table 14 accompanying and forming the part of this specification. It is observed that the enzyme is active between 30 to 70° C.

TABLE 14

| Optimum Temperature for Protease | |
|---|---|
| Temperature (° C.) | Relative Activity (%) |
| 30 | 23.38 |
| 40 | 60.83 |
| 50 | 100.00 |
| 60 | 61.98 |
| 70 | 25.09 |

Example 37

This example illustrates the pH range in which the protease secreted by the said strain is stable. The influence of pH on stability of the enzyme was studied where pH of the enzyme was adjusted with following buffers: (citrate-pH 3, 4 and 5; citrate phosphate buffer-pH 6; phosphate buffer-pH 7; Tris HCl buffer-pH 8; carbonate bicarbonate-pH 9 and 10 and sodium phosphate-NaOH pH 11.0) and incubated for 1 h at 28° C. The residual activity of the enzyme after incubation was assayed at 50° C. pH 9. The results are illustrated in Table 15 wherein it is observed that the enzyme is stable in the range of pH 3 to 11, with maximum stability at pH 7.

TABLE 15

| pH Stability of Protease | |
|---|---|
| pH | Residual Activity (%) |
| 3 | 81.56 |
| 4 | 88.35 |
| 5 | 94.62 |
| 6 | 97.57 |
| 7 | 100.00 |
| 8 | 99.29 |
| 9 | 89.97 |
| 10 | 88.06 |
| 11 | 85.55 |

Example 38

This example illustrates the temperature range in which the protease secreted by the said strain is stable for 1 h. For determining the temperature stability, crude protease was incubated in 0.1 M potassium phosphate buffer pH 7.0 at temperatures ranging from 4 to 70° C. for 1 h and the residual activity was measured at 50° C., pH 9. The results are illustrated in Table 16 wherein it is observed that the enzyme is stable up to 50° C.

TABLE 16

| Temperature Stability of Protease | |
|---|---|
| Temperature (° C.) | Residual Activity (%) |
| 4 | 100.00 |
| 20 | 99.25 |
| 30 | 97.87 |
| 40 | 84.97 |
| 50 | 62.17 |
| 60 | 11.51 |
| 70 | 6.66 |

Example 39

Stability of the said protease was also determined at 50° C. with respect to time by incubating the crude protease in carbonate bicarbonate buffer pH 9.0 at 50° C. up to 2 h. Aliquots were removed at regular intervals of 15 min and residual activity was estimated at 50° C., pH 9. The results are illustrated in Table 17 wherein the half life of the protease at 50° C. was found to be approximately 2 h.

TABLE 17

| Temperature Stability of Protease at pH 9.0 and 50° C. | |
|---|---|
| Time (min) | Residual Activity (%) |
| 0 | 100.00 |
| 15 | 93.55 |
| 30 | 83.14 |
| 45 | 74.75 |

TABLE 17-continued

Temperature Stability of Protease at pH 9.0 and 50° C.

| Time (min) | Residual Activity (%) |
|---|---|
| 60 | 64.19 |
| 75 | 59.30 |
| 90 | 55.61 |
| 105 | 52.33 |
| 120 | 50.36 |

Example 40

This example illustrates the determination of activity of the protease from *Beauveria* sp. MTCC 5184 towards azocoll. The reaction mixture contained an aliquot of suitably diluted protease and 10 mg azocoll in 0.05M Tris HCl buffer pH 8.0 in a total volume of 2.5 ml. Heat inactivated enzyme (by boiling for 15 min) was taken as blank. After incubation at 37° C. for 10 min, the reaction was terminated by filtering through Whatman No. 1 filter paper. The absorbance of filtrate was measured at 580 nm. One unit of enzyme activity is defined as the amount of enzyme required to cause an increase in absorbance by one unit at 580 nm per minute. The crude culture filtrate grown as described in Example 2 had an azocoll activity of 4.31 U/ml. The purified protease as described in Example 22 having caseonolytic activity of 20.7 U/ml showed azocoll activity of 1.84 U/ml.

Example 41

This example illustrates the determination of activity of the protease from *Beauveria* sp. MTCC 5184 towards elastin-orcin. The reaction mixture contained an aliquot of suitably diluted protease enzyme and 20 mg elastin-orcin in 0.1M sodium carbonate buffer pH 9.0 in a total volume of 3 ml. Heat inactivated enzyme (by boiling for 15 min) was taken as blank. After incubation at 50° C. for 30 min, the reaction was terminated by addition of 2 ml 0.7M phosphate buffer pH 6. Contents were centrifuged and absorbance of the supernatant was measured at 578 nm. One unit of enzyme activity is defined as the amount of enzyme required to cause an increase in absorbance by one unit at 578 nm in one minute. The crude culture filtrate grown as described in Example 2 showed an activity of 0.012 U/ml. The purified protease as described in Example 22 having caseonolytic activity of 20.7 U/ml showed activity of 0.011 U/ml against elastin-orcin.

Example 42

This example illustrates the determination of activity of the protease from *Beauveria* sp. MTCC 5184 towards azocasein. The reaction mixture contained an aliquot of suitably diluted protease and 1 mg azocasein in 0.05 M sodium carbonate buffer pH 9.0 in a total volume of 500 µl. Heat inactivated enzyme (by boiling for 15 min) was taken as blank. After incubation at 50° C. for 30 min, the reaction was terminated by addition of 500 µl of 10% TCA. After cooling on ice for 15 min, contents were centrifuged at 8000 rpm for 10 min. To 800 µl of supernatant, 200 µl of 1.8M NaOH was added and absorbance was measured at 420 nm. One unit of enzyme activity is defined as the amount of enzyme required to cause an increase in absorbance by one unit at 420 nm per minute. The crude culture filtrate grown as described in Example 2 showed an activity of 16.05 U/ml.

Example 43

This example illustrates the determination of activity of the purified protease from *Beauveria* sp. MTCC 5184 towards N-α-benzoyl-DL-arginine-p-nitroanilide (BAPNA). The reaction mixture contained an aliquot of suitably diluted protease in 0.1M sodium carbonate buffer pH 9.0 in a total volume of 500 µl. 500 µl of 1.5 mM BAPNA prepared in 0.1M sodium carbonate buffer pH 9.0 was added and incubated at 50° C. for 60 min. The reaction was terminated by addition of 250 µl of 10% acetic acid. Absorbance of the supernatant was measured at 410 nm. One unit of activity is defined as the amount of enzyme required to cause an increase in absorbance by one unit at 410 nm in one minute. The protease purified as described in Example 22 having caseonolytic activity of 20.7 U/ml showed an activity of 0.018 U/ml.

Example 44

This example illustrates the non-collagenase nature of the protease from *Beauveria* sp MTCC 5184 by fluorescence studies using NMITLI-1 and Collagenase-1 substrates. Initially fluorescence experiments were done with crude as well as purified proteases against NMITLI-1 substrate. Fluorescence experiments were carried out in triethanolamine buffer (TEA) pH 8 at room temperature. Typically, the assay contained 290 µl of 100 mM TEA buffer pH 8, having NMITLI-1 substrate concentration of 1.8 µM (100 of 112 µM stock solution). The reaction was initiated by adding 5 µl of enzyme samples. The excitation wavelength was 340 nm and the emission was scanned from 425-625 nm, at different intervals of time. There was three fold increase in the fluorescence of AEDANS chromophore (+++) indicating proteolytic nature of the enzyme samples.

```
NMITLI-I

Dabcyl-Gaba-Arg-Pro-Leu-Gly-Ala-Ala-Ala-Lys-Val-Gaba-Cys-Lys-NH₂ (SEQ ID NO: 12)
                                                          |
                                                        AEDANS
```

Crude as well as purified proteases samples showing activity against NMITLI-1 substrate, were also screened for collagenase activity with Collagenase substrate-I. Fluorescence experiments were carried out in triethanolamine buffer (TEA) pH 8 at room temperature. Typically, the assay contained 290 µl of 100 mM TEA buffer pH 8, having substrate (Collagenase substrate-I) concentration of 1.6 µM (5 µl of 80 mM stock solution). The reaction was initiated by adding 5 µl of enzyme samples. The excitation wavelength was 340 nm and the emission was scanned from 425-625 nm, at different intervals of time. There is no increase in the fluorescence of AEDANS chromophore (−) indicating absence of collagenase activity.

```
Collagenase substrate-I
Dabcyl-Gaba-Lys-Gly-Gly-Pro-Leu-Gly-Pro-Pro-Gly-Pro-Gly-Gly-Cys-Lys-NH₂ (SEQ ID NO: 13)
                                                            |
                                                          AEDANS
```

Example 45

This example illustrates the stability of *Beauveria* sp MTCC 5184 protease in presence of detergents. The crude protease was incubated with detergents (0.7 mg/ml final concentration) at 40° C. up to 1 h. Detergents were heated at 100° C. for 10 min before use. Samples were removed at intervals of 15 min and residual activity was measured and expressed as percentage of initial activity with respective detergents taken as 100%. The protease was stable in the presence of all detergents and retained 75-100% activity after 1 h depending on the detergent (Table 18).

TABLE 18

Stability of protease in presence of detergents

| Detergent (0.7 mg/ml) | Residual Activity (%) | | | | |
|---|---|---|---|---|---|
| | 0 mm | 15 min | 30 min | 45 min | 60 min |
| Nil | 100.00 | 82.16 | 90.25 | 78.74 | 82.54 |
| Aerial | 100.00 | 93.59 | 95.56 | 98.28 | 100.64 |
| Fena | 100.00 | 91.15 | 100.87 | 89.74 | 88.03 |
| Rin | 100.00 | 88.18 | 100.25 | 76.46 | 79.47 |
| Surf excel | 100.00 | 87.52 | 96.14 | 77.95 | 78.64 |

Example 46

This example illustrates the effect of water miscible as well as water immiscible organic solvents on stability of purified protease at 28° C. Following organic solvents were used: acetone, 1-butanol, benzene, chloroform, dimethylsulphoxide, ethanol, hexane, isopropanol and methanol. Purified protease was incubated at 28° C., pH 7 with 25% (v/v) organic solvents (effective concentration). Samples were removed at different time intervals and residual activity was estimated. Sample without organic solvent served as control. Initial activity with respective solvents was taken as 100% (Table 19). The protease was highly stable in presence of organic solvents with the exception of acetone, benzene, chloroform and hexane which showed less than 30% residual activity while more than 80% activity was retained in ethanol, isopropanol, methanol, butanol and dimethylsulphoxide after 24 h (Table 19). Control without solvent showed around 26.66% residual activity under identical conditions.

Example 48

Figure 11:
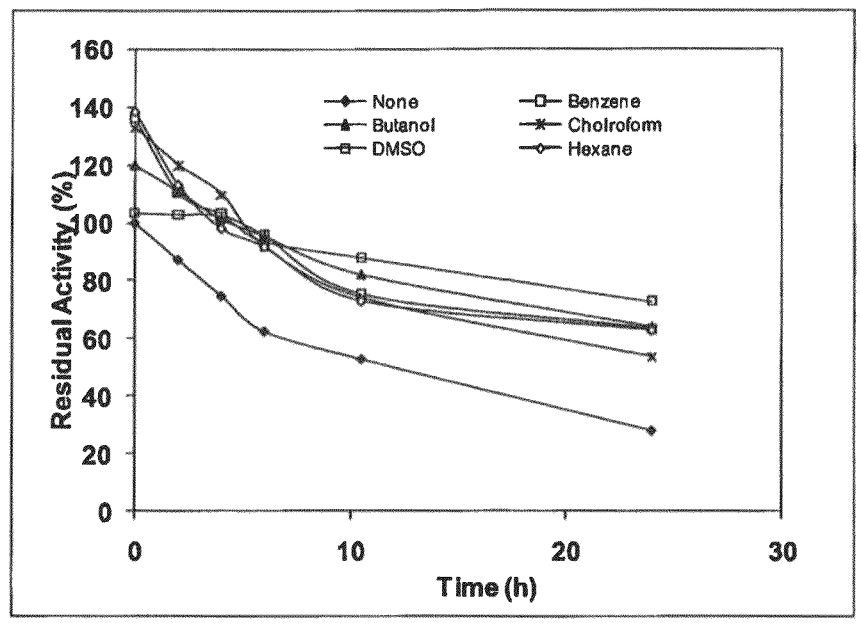

This example illustrates the effect of water immiscible organic solvents on stability of crude protease at 37° C. Following organic solvents were used: 1-butanol, benzene, chloroform, dimethylsulphoxide and hexane. Crude protease was incubated at 37° C., pH 7 with 25% (v/v) organic solvents (effective concentration). Samples were removed at different time intervals and residual activity was estimated. Sample without organic solvent served as control and initial activity for respective solvent was taken as 100% (FIG. 11). The protease was highly stable in presence of water immiscible organic solvents and stability was more or less similar for all the solvents tested. More than 80% activity was retained after 12 h which decreased to 50-80% after 24 h incubation while control retained less than 40% activity after 24 h.

Example 49

This example illustrates the effect of water miscible as well as water immiscible organic solvents on stability of purified protease at 50° C. Following organic solvents were used: acetone, 1-butanol, benzene, chloroform, dimethylsulphoxide, ethanol, hexane, isopropanol and methanol. Purified protease was incubated at 50° C., pH 7 with 25% (v/v) organic solvents (effective concentration). Samples were removed at different time intervals and residual activity was estimated. Sample without organic solvent served as control and initial activity for respective solvent was taken as 100% (Table 20). The protease was highly stable up to 1 h in presence of all the organic solvents with residual activities ranging from 60 to 90%. After 2 h, stability was maximum in acetone and DMSO with residual activities of around 70% while in all other solvents, residual activity was around 30-40%.

TABLE 20

Stability of protease in presence of organic solvents at 50° C.

| Type of the solvent | Solvent | Residual Activity (%) | | |
|---|---|---|---|---|
| | | 0 h | 1 h | 2 h |
| Control | Nil | 100.00 | 69.03 | 35.87 |
| Water miscible | Acetone | 100.00 | 99.07 | 70.45 |
| | Ethanol | 100.00 | 98.50 | 45.21 |
| | Isopropanol | 100.00 | 71.26 | 46.16 |
| | Methanol | 100.00 | 93.49 | 46.09 |
| Water immiscible | Benzene | 100.00 | 61.85 | 40.66 |
| | Butanol | 100.00 | 82.07 | 46.38 |
| | Chloroform | 100.00 | 77.14 | 38.55 |
| | DMSO | 100.00 | 87.52 | 72.14 |
| | Hexane | 100.00 | 76.18 | 29.43 |

Example 50

This example illustrates the effect of β-mercapto ethanol (BME) and Triton X-100 on protease activity of *Beauveria* sp MTCC 5184. 10 μM of purified protease in 50 mM phosphate buffer pH 7 was pre-incubated with 1 to 10% (v/v) β-mercapto ethanol (BME), 0.2 to 2% Triton X-100 at 28° C. for 30 min. Residual activity was measured at 50° C., pH 9.0 and expressed as percentage of activity without any denaturants (control) taken as 100%. Protease from *Beauveria* sp MTCC 5184 retained full activity in 10% BME indicating the absence of disulphide bonds in the enzyme while 80% activity was retained in presence of 2% Triton X-100.

Example 51

Figure 12:
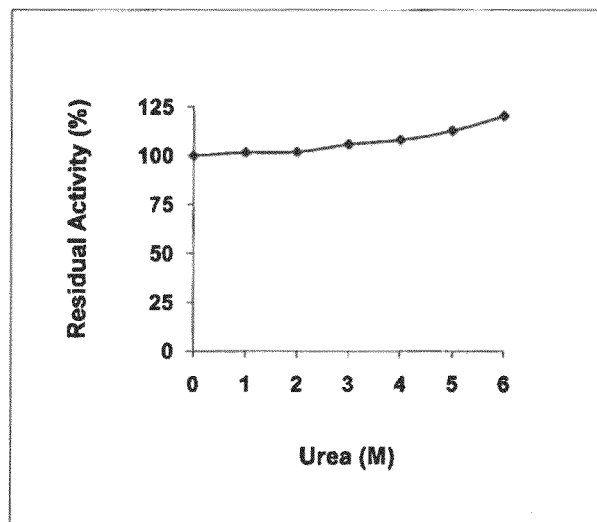
Figure 13:
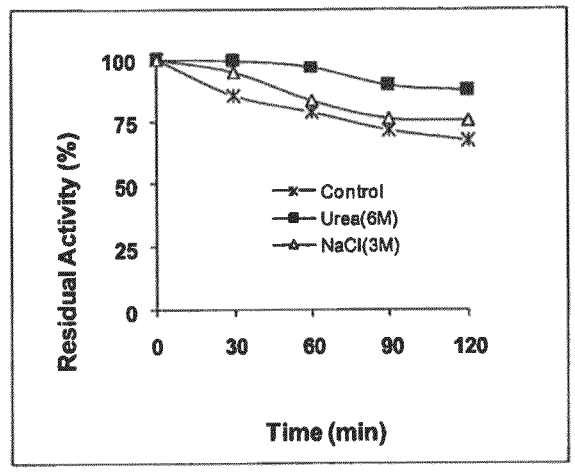

This example illustrates the effect of urea on protease activity of *Beauveria* sp MTCC 5184. Stability was checked under two sets of conditions, a) 10 μM of purified protease in 50 mM phosphate buffer pH 7 was pre-incubated with 1 to 6M urea at 28° C. for 30 min, b) 10 μM of purified protease in 50 mM phosphate buffer pH 7 was pre-incubated with 6M urea at 28° C. up to 2 h. Samples were removed at regular intervals and residual activity was measured at 50° C., pH 9.0 and expressed as percentage of activity without urea taken as 100%. Protease from *Beauveria* sp MTCC 5184 was stable in presence of urea and showed slight increase with increasing concentration of urea up to 6M (FIG. 12). In presence of 6M urea, protease was stable up to 2 h and retained more than 85% of initial activity (FIG. 13).

Example 52

Figure 14:
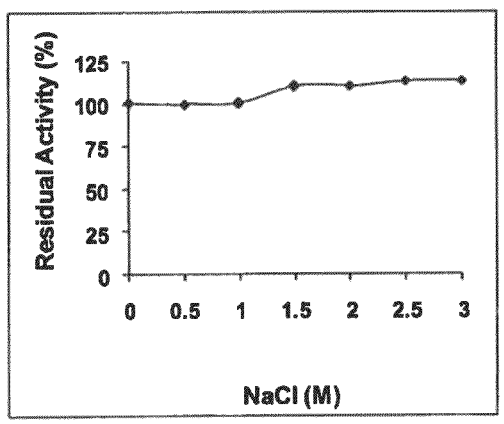

This example illustrates the effect of NaCl on purified protease activity of *Beauveria* sp MTCC 5184. Stability was checked under two sets of conditions, a) 10 μM of purified protease in 50 mM phosphate buffer pH 7 was pre-incubated with 0.5 to 3M NaCl at 28° C. for 30 min, b) 10 μM of purified protease in 50 mM phosphate buffer pH 7 was pre-incubated with 3M NaCl at 28° C. up to 2 h. Samples were removed at regular intervals and residual activity was measured at 50° C., pH 9.0 and expressed as percentage of activity without NaCl taken as 100%. Protease from *Beauveria* sp MTCC 5184 was stable in presence of NaCl and showed slight increase with increasing concentration of NaCl up to 3M (FIG. 14). In presence of 3M NaCl, protease was stable up to 2 h and retained around 75% of initial activity (FIG. 13).

Example 53

This example illustrates the pH range in which the xylanase secreted by the said strain is active and stable. For determination of optimum pH for xylanase, the enzyme was diluted in the following buffers (0.05M) and assayed at 50° C. for 30 minutes: Citrate (pH 3, 4 and 5) citrate phosphate buffer (pH 6), phosphate buffer (pH 7), Tris HCl buffer (pH 8) and carbonate bicarbonate (pH 9). For stability studies, xylanase was pre-incubated in above buffers at room temperature for 1 h and residual activity was assayed at 50°, pH 6 for 30 min. The results are presented in accompanying Table 21 and forming the part of this specification. It is observed that the enzyme is active between pH 4 and 9 and stable in the pH range of 3 to 9.

TABLE 21

Optimum pH and pH stability of Xylanase from *Beauveria* sp MTCC 5184

| pH | Optimum pH Relative Activity (%) | pH stability Residual Activity (%) |
|---|---|---|
| 3 | 7.33 | 48.62 |
| 4 | 40.57 | 87.19 |
| 5 | 87.19 | 91.17 |
| 6 | 100 | 94.24 |
| 7 | 67.30 | 100 |
| 8. | 41.29 | 86.99 |
| 9 | 27.64 | 61.43 |

Example 54

This example illustrates the temperature range in which the xylanase secreted by the said strain is active. For determination of optimum temperature for xylanase, the enzyme was estimated at pH 6 and at temperatures ranging from 30 to 70° C. The results of the experiment have been illustrated in Table 22 accompanying and forming the part of this specification. It is observed that the enzyme is active between 30 to 70° C.

TABLE 22

Optimum Temperature of Xylanase from *Beauveria* sp MTCC 5184

| Temperature (° C.) | Relative Activity (%) |
|---|---|
| 30 | 42.76 |
| 40 | 84.40 |
| 45 | 91.77 |
| 50 | 100 |
| 55 | 84.40 |
| 60 | 49.66 |
| 70 | 26.50 |

Example 55

This example illustrates the pH range in which the amylase secreted by the said strain is active and stable. For determination of optimum pH for amylase, the enzyme was diluted in the following buffers (0.05M) and assayed at 50° C. for 30 minutes: Citrate (pH 3, 4 and 5) citrate phosphate buffer (pH 6), phosphate buffer (pH 7), Tris HCl buffer (pH 8) and carbonate bicarbonate (pH 9). For stability studies, amylase was pre-incubated in above buffers at room temperature for 1 h and residual activity was assayed at 50°, pH 6 for 30 min. The results are presented in accompanying Table 23 and forming the part of this specification. It is observed that the enzyme is active in the pH range 4 and 8 and stable in the pH range of 3 to 9.

TABLE 23

Optimum pH and pH stability of Amylase from *Beauveria* sp MTCC 5184

| pH | Optimum pH Relative Amylase Activity (%) | pH stability Residual Amylase Activity (%) |
|---|---|---|
| 3 | 6.93 | 40.70 |
| 4 | 63.42 | 82.00 |
| 5 | 89.77 | 89.66 |
| 6 | 100 | 95.83 |
| 7 | 76.15 | 100 |
| 8. | 24.39 | 97.75 |
| 9 | 8.03 | 95.21 |

Example 56

This example illustrates the temperature range in which the amylase secreted by the said strain is active. For determination of optimum temperature, amylase was estimated at pH 6 and at temperatures ranging from 20 to 70° C. The results of the experiment have been illustrated in Table 24 accompanying and forming the part of this specification. It is observed that the enzyme is active in the temperature range of 20 to 70° C.

TABLE 24

Optimum Temperature of Amylase from *Beauveria* sp MTCC 5184

| Temperature (° C.) | Relative Activity (%) |
|---|---|
| 20 | 61.13 |
| 30 | 72.53 |
| 40 | 79.64 |
| 45 | 100 |

TABLE 24-continued

Optimum Temperature of Amylase from *Beauveria* sp MTCC 5184

| Temperature (° C.) | Relative Activity (%) |
|---|---|
| 50 | 86.02 |
| 55 | 71.16 |
| 60 | 45.31 |
| 70 | 21.92 |

Example 57

This example illustrates the pH range in which the lipase secreted by the said strain is active. For determination of optimum pH for lipase, the enzyme was diluted and assayed at 50° C. and pH ranging from 4 to 9 by titrimetric method. Following buffers were used: acetate (pH 4 and 5) citrate (pH 6), phosphate (pH 7), Tris HCl (pH 8) and carbonate bicarbonate (pH 9). The results are presented in accompanying Table 25 and forming the part of this specification. It is observed that the enzyme is active between pH 4 and 9.

TABLE 25

Optimum pH and pH stability of lipase from *Beauveria* sp MTCC 5184

| pH | Relative Activity (%) |
|---|---|
| 4 | 8.99 |
| 5 | 18.26 |
| 6 | 72.75 |
| 7 | 100 |
| 8 | 27.25 |
| 9 | 13.62 |

Example 58

This example illustrates the temperature range in which the lipase secreted by the said strain is active. For determination of optimum temperature, lipase activity was determined by titrimetric method at pH 7 and at temperatures ranging from 20 to 60° C. The results of the experiment have been illustrated in Table 26 accompanying and forming the part of this specification. It is observed that the enzyme is active between 20 to 60° C.

TABLE 26

Optimum Temperature of lipase from *Beauveria* sp MTCC 5184

| Temperature (° C.) | Relative Activity (%) |
|---|---|
| 20 | 34.94 |
| 30 | 49.79 |
| 40 | 55.97 |
| 50 | 100 |
| 60 | 50.52 |

Example 59

Figure 15:
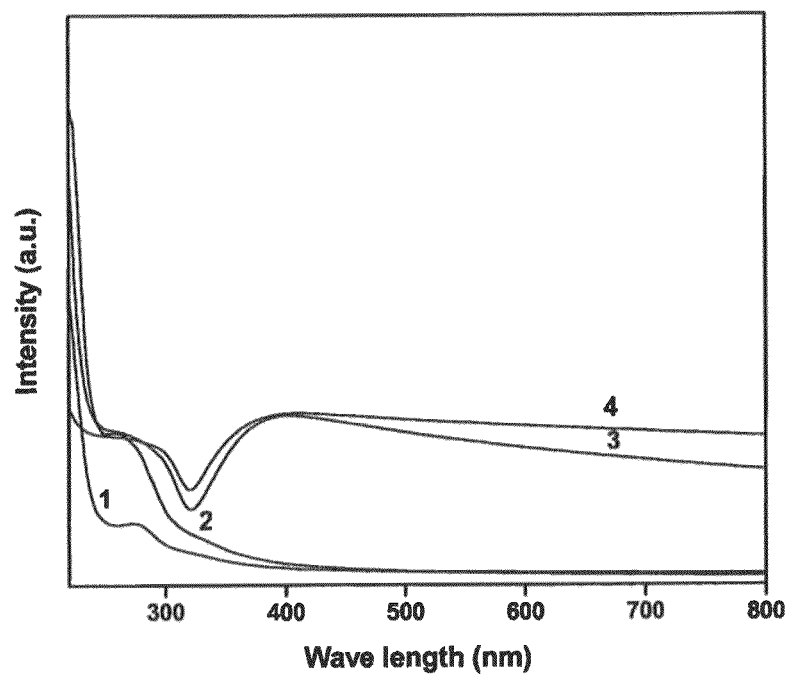

This example illustrates the removal of silver from waste X-ray film and synthesis of silver nanoparticles by using crude and purified proteases as well as biomass filtrate of *Beauveria* sp. MTCC 5184. Fungus was grown aerobically in MGYP broth whose composition is (grams per liter): malt extract-3, yeast extract-3, peptone-5, glucose-10 at 28° C., 200 rpm for 48 h. The biomass was harvested by centrifugation, followed by extensive washing with distilled water to remove medium components. 10 g of washed biomass (wet weight) was incubated with 100 ml of Milli-Q deionized water at 28° C., 200 rpm. After 2 h incubation, biomass was filtered on Whatman No. 1 filter paper and filtrate was collected. For removal of silver and synthesis of silver nanoparticles, 5 g of washed X-ray film cut into 2 cm×2 cm pieces was incubated crude protease, purified protease and biomass filtrate in a total volume of 100 ml at 28° C. and 200 rpm. Removal of silver containing protein (gelatin) layer and nanoparticle synthesis was monitored visually as well as by UV-Vis spectroscopy up to 48 h. Complete removal of gelatin layer with simultaneous appearance of clean film along with presence of nanoparticles was observed within 24 h. Silver nanoparticles could be synthesized by crude as well as purified protease and also biomass filtrate. Biomass filtrate is preferred since crude protease contains media constituents as contaminants and use of purified protease will be costly. Silver nanoparticles synthesized were characterized by UV-Visible spectroscopy (FIG. 15), Transmission electron microscopy (TEM), diffraction pattern of single nanoparticle Fourier Transformation Infrared Spectroscopy and X-ray diffraction.

Example 60

Figure 16:
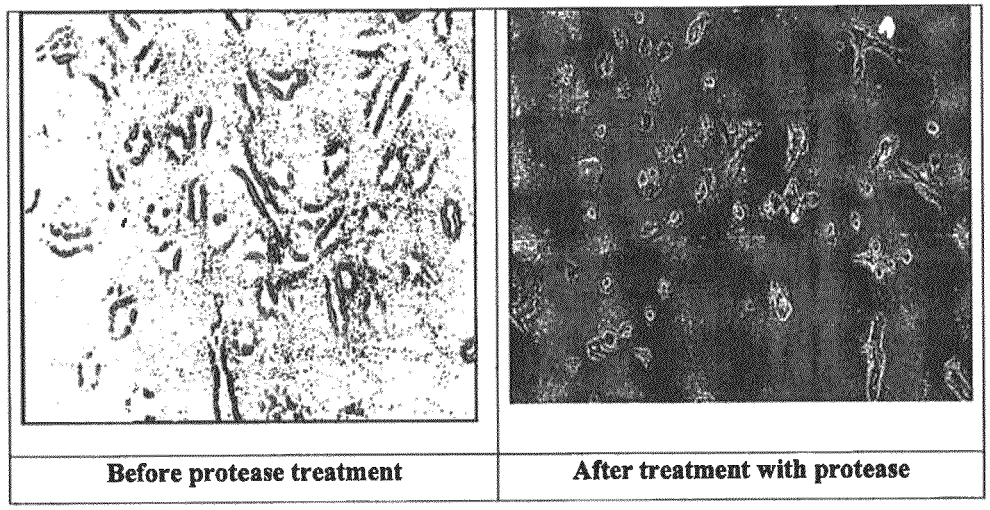

This example illustrates the application of purified protease in animal tissue culture for the separation of cells. The cells were grown on endothelial cells basal medium-2 (EBM-2). After 48 h of growth, medium was removed from plate in a falcan tube. The adherent cells at the bottom of the plate were washed with 2 ml of 1 mM EDTA solution followed by addition of 200 μg of protease in 4 ml of 1 mM EDTA solution and incubated at 37° C. for 2 min. Cells were flushed out, collected in falcan tube and spinned at 2000 rpm for 2 min. The supernatant was removed and cell pellet was re-suspended in 1 ml fresh medium and transferred to new petri plate. Microscopic observation showed the separated cells which was due to the action of protease (FIG. 16).

Example 61

Figure 17:
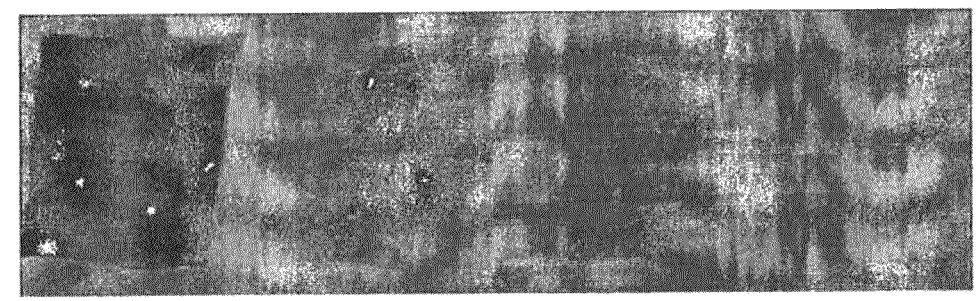

This example describes the application of protease in detergent formulation. A piece of white cloth was dipped in blood and air dried. The blood stained cloth was cut into four equal parts of 0.5 g each and dipped in 2% formaldehyde for 2 min in 4 different petri plates and rinsed with water to remove excess formaldehyde. The pieces were dipped in 30 ml of reaction mixture and incubated at 28-30° C. for 30 min under different conditions: (a) control (only water) (b) Only detergent (c) Only crude protease (8.5 U/ml) and (d) detergent+ crude protease (8.5 U/ml). The cloth pieces were rinsed 4 times with tap water. The washing performance was best where detergent and protease was used together. Blood clots were not removed with only detergent while protease alone was able to remove blood stain along with clots (FIG. 17).

Example 62

This example illustrates the process for unhairing of goat and sheep skins using crude *Beauveria* MTCC 5184 protease. The protease produced as described in Example 6B was subjected to ammonium sulphate precipitation (90% saturation) and used for dehairing studies. Wet salted goat and sheep skins were taken and soaked for 6 hours. After soaking the weight of the skin were noted. A paste of 3% protease and 10% water based on the soaked weight was applied on the flesh side of the skin and piled 5-10 hours. A corresponding chemical based control process was also carried out using paste of 10% lime, 3% sulfide and 15% water. Then both control and experimental skins were unhaired and the unhairing efficacy of experimental skins ranged from 85 to 100% which was similar to the chemical based process. The pelts were clean and free from scud. The dehaired pelts were processed into crust leathers and the quality of the crust leathers was also assessed. The quality of leather as evaluated by tensile strength, tear strength and grain bursting strength were comparable to that obtained by lime and sulphide method of dehairing. The reduction in pollution load was also assessed by analyzing the various waste streams of both control and experimental process. The results indicate significant reduction in COD and sulfide with BOD/COD ratio of 0.69 where protease was used for dehairing which indicates that the degradability and treatability of the wastewater is much better compared to the wastewater of chemical process system.

Example 63

This example illustrates the process for unhairing of cow hides using crude Beauveria MTCC 5184 protease. The protease produced as described in Example 6B was subjected to ammonium sulphate precipitation (90% saturation) and used for dehairing studies. Wet salted cow hides were taken and soaked for 8 hours. After soaking the weight of the hides were noted. The hides were treated in drums using 15% water and 4% enzyme. A corresponding chemical based control process was also carried out using 150% water, 10% lime and 3% sodium sulfide. Next day the skins were unhaired and the unhairing efficacy ranged from 70 to 100%. The pelts were clean and free from scud. The dehaired pelts were processed into crust leathers and the quality of the crust leathers was also assessed. The quality of leather as evaluated by tensile strength, tear strength and grain bursting strength were comparable to that obtained by lime and sulphide method of dehairing. The reduction in pollution load was also assessed by analyzing the various waste streams of both control and experimental process. The results indicate significant reduction in COD and sulfide with BOD/COD ratio of 0.72 where protease was used for dehairing which indicates that the degradability and treatability of the wastewater is much better compared to the wastewater of chemical process system.

The main advantages of the present invention are the following:

The fungal strain is a new isolate.
The fungal strain described in the present invention is able to produce protease singly and in association with amylase, lipase and xylanase.
The fungal strain described in the present invention is able to produce protease amylase, lipase and xylanase singly or in combination.
Both submerged as well as solid state fermentation can be employed for enzyme production.
These cocktail of enzymes have many industrial applications such as leather, textile, detergent and food industries.
The protease has already been evaluated for its applications in pre-tanning operations in leather industry.
The crude protease can dehair animal skins/hides without the requirement of any added chemicals like lime and sulphide.
The protease is capable of separating endothelial cells and can be used in animal cell culture.
The protease is capable of synthesizing nanoparticles.
The crude protease preparation has broad substrate specificity and can degrade variety of proteins such as albumin, hemoglobin, gelatin, keratins as required for applications in leather and detergent industries.
The protease has stability over wide pH range of 3 to 10 and also in presence of detergents making it a suitable candidate for its application in detergent and allied industries.
The protease is stable in the presence of various water miscible and water immiscible solvents, making it suitable for enzymatic synthesis of various molecules in organic solvents.

We claim:

1. An isolated fungal strain *Beauveria* species bearing accession number MTCC 5184, wherein the said strain is deposited at MTCC, an International Depository recognized under the Budapest Treaty.

* * * * *

SEQUENCE LISTING

<160> NUMBER OF SEQ ID NOS: 25

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtagtcatat gcttgtctc                                                    19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tccgcaggtt cacctacgga                                                   20

```
<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tccgtaggtg aacctgcgg                                                   19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcctccgctt attgatatgc                                                  20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggctgctggc accagacttg c                                                21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcaagtctgg tgccagcagc c                                                21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cttccgtcaa ttcctttaag                                                  20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aacttaaagg aattgacgga ag                                               22

<210> SEQ ID NO 9
```

-continued

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcatcacaga cctgttattg cctc                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaggcaataa caggtctgtg atgc                                          24

<210> SEQ ID NO 11
<211> LENGTH: 16
<212> TYPE: PRT
<213> ORGANISM: Beauveria sp.

<400> SEQUENCE: 11

Ala Met Ala Thr Pro His Val Ala Pro Leu Val Leu Tyr Gly Val Ala
1               5                   10                  15

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dabcyl-Gaba
<220> FEATURE:
<221> NAME/KEY: MOD_RES
<222> LOCATION: (11)..(11)
<223> OTHER INFORMATION: Gaba
<220> FEATURE:
<221> NAME/KEY: MOD_RES
<222> LOCATION: (12)..(12)
<223> OTHER INFORMATION: Cys-AEDANS
<220> FEATURE:
<223> OTHER INFORMATION: C-term NH2

<400> SEQUENCE: 12

Xaa Arg Pro Leu Gly Ala Ala Ala Lys Val Xaa Cys Lys
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dabcyl-Gaba
<220> FEATURE:
<221> NAME/KEY: MOD_RES
<222> LOCATION: (14)..(14)
<223> OTHER INFORMATION: Cys-AEDANS
```

```
<220> FEATURE:
<223> OTHER INFORMATION: C-term NH2

<400> SEQUENCE: 13

Xaa Lys Gly Gly Pro Leu Gly Pro Pro Gly Pro Gly Gly Cys Lys
1               5                   10                  15

<210> SEQ ID NO 14
<211> LENGTH: 12
<212> TYPE: PRT
<213> ORGANISM: Magnaporthe poae

<400> SEQUENCE: 14

Met Ala Thr Pro His Val Ser Gly Leu Val Leu Tyr
1               5                   10

<210> SEQ ID NO 15
<211> LENGTH: 12
<212> TYPE: PRT
<213> ORGANISM: Aspergillus niger

<400> SEQUENCE: 15

Met Ala Thr Pro His Val Thr Gly Leu Ile Leu Tyr
1               5                   10

<210> SEQ ID NO 16
<211> LENGTH: 12
<212> TYPE: PRT
<213> ORGANISM: Verticillium dahliae

<400> SEQUENCE: 16

Met Ala Ser Pro His Val Ala Gly Leu Val Val Tyr
1               5                   10

<210> SEQ ID NO 17
<211> LENGTH: 12
<212> TYPE: PRT
<213> ORGANISM: Metarhizium anisopliae

<400> SEQUENCE: 17

Met Ala Ser Pro His Val Ala Gly Leu Ala Leu Tyr
1               5                   10

<210> SEQ ID NO 18
<211> LENGTH: 12
<212> TYPE: PRT
<213> ORGANISM: Acremonium chrysogenum

<400> SEQUENCE: 18

Met Ala Thr Pro His Val Thr Gly Val Val Leu Tyr
1               5                   10

<210> SEQ ID NO 19
<211> LENGTH: 12
<212> TYPE: PRT
<213> ORGANISM: Epichloe festucae

<400> SEQUENCE: 19

Met Ala Thr Pro His Val Val Gly Leu Ala Leu Tyr
1               5                   10

<210> SEQ ID NO 20
<211> LENGTH: 12
<212> TYPE: PRT
<213> ORGANISM: Neotyphodium lolii
```

```
<400> SEQUENCE: 20

Met Ala Thr Pro His Val Val Gly Leu Ala Leu Tyr
1               5                   10

<210> SEQ ID NO 21
<211> LENGTH: 12
<212> TYPE: PRT
<213> ORGANISM: Hypocrea lixii

<400> SEQUENCE: 21

Met Ala Thr Pro His Val Val Gly Leu Ala Leu Tyr
1               5                   10

<210> SEQ ID NO 22
<211> LENGTH: 12
<212> TYPE: PRT
<213> ORGANISM: Trichoderma hamatum

<400> SEQUENCE: 22

Met Ala Thr Pro His Val Val Gly Leu Ala Leu Tyr
1               5                   10

<210> SEQ ID NO 23
<211> LENGTH: 12
<212> TYPE: PRT
<213> ORGANISM: Hypocrea virens

<400> SEQUENCE: 23

Met Ala Thr Pro His Val Val Gly Leu Ala Leu Tyr
1               5                   10

<210> SEQ ID NO 24
<211> LENGTH: 14
<212> TYPE: PRT
<213> ORGANISM: Pseudoalteromonas flavipulchra

<400> SEQUENCE: 24

Met Ala Thr Pro His Val Ala Gly Ala Ala Ala Leu Val Leu
1               5                   10

<210> SEQ ID NO 25
<211> LENGTH: 12
<212> TYPE: PRT
<213> ORGANISM: Hypsizygus marmoreus

<400> SEQUENCE: 25

Met Ala Thr Pro His Ile Ala Gly Leu Val Ala Tyr
1               5                   10
```